US006831207B1

(12) United States Patent
Grimm et al.

(10) Patent No.: US 6,831,207 B1
(45) Date of Patent: Dec. 14, 2004

(54) DNA SEQUENCES ENCODING FOR SUBUNIT CHLD OF PLANT MAGNESIUM CHELATASES AND DETERMINING THE ACTIVITY OF PLANT MAGNESIUM CHELATASES

(75) Inventors: Bernhard Grimm, Gatersleben (DE); Jutta Papenbrock, Hannover (DE); Frank Hänel, Jena (DE); Susanna Gräfe, Jena (DE); Frank Schmidt, Frankfurt (DE); Wolfgang Streber, Bad Soden (DE)

(73) Assignee: Hoechst Schering AgrEvo, Berlin (DE)

( * ) Notice: Subject to any disclaimer, the term of this patent is extended or adjusted under 35 U.S.C. 154(b) by 0 days.

(21) Appl. No.: 09/403,463
(22) PCT Filed: Apr. 27, 1998
(86) PCT No.: PCT/EP98/02483
§ 371 (c)(1),
(2), (4) Date: Oct. 21, 1999
(87) PCT Pub. No.: WO98/49330
PCT Pub. Date: Nov. 5, 1998

(30) Foreign Application Priority Data

Apr. 25, 1997 (DE) .......................................... 197 17 656

(51) Int. Cl.$^7$ ............................. A01H 5/00; C12Q 1/68
(52) U.S. Cl. ......................... 800/298; 435/6; 435/69.1; 435/183; 435/419; 435/252.1; 435/254.11; 435/320.1; 536/23.6
(58) Field of Search ........................ 536/23.6; 530/370; 800/295, 298; 435/320.1, 69.1, 419, 252.1, 254.11, 6, 183

(56) References Cited

PUBLICATIONS

Jensen et al (1996) Mol. Gen. Genet. 250:383–393.*
Papenbrock et al (1997) The Plant Journal 12:981–990.*
Jensen et al (1996) Mol. Gen. Genet. 250:383–393.*
Luo et al, Database GenEMBL, Accession No. AF014399, Oct. 7, 1997.*
Jensen et al (1996) J. Biol. Chem. 271:16662–16667.*
Kannangara et al (1997) Mol. Gen. Genetics (Mar. 18, 1997) 254:85–92.*
Jensen et al., "Structural genes for Mg–chelatase subunits in barley: Xantha–f, –g and –h", Molecular and General Genetics, vol. 250, pp. 383–394, 1996.
Gibson et al., "A Putative Mg Chelatase Subunit from Arabidopsis thaliana cv C24", Plant Physiology, vol. 111, pp. 61–71, 1996.
Nakayama et al., "Cloning, Subcellular Localization and Expression of CHLI, A Subunit of Magnesium–Chelatase in Soybean", Biochemical and Biophysical Research Communications, vol. 215, No. 1, pp. 422–428, 1995.
Kannangara et al., "Magnesium chelatase: association with ribosomes and mutant complementation studies identify barley subunit Xantha–G as a functional counterpart of Rhodobacter subunit BchD", Molecular and General Genetics, vol. 254, pp. 85–92.
Gibson et al., "Magnesium–protoporphyrin chelatase of Rhodobacter sphaeroides: Reconstitution of activity by combining the products of the bchH, –I, and –D genes expressed in *Escherichia coli*", Proceedings of the National Academy of Sciences of the USA, vol. 92, pp. 1941–1944, Mar. 1995.
Hudson et al., "Olive: a key gene required for chlorophyll biosynthesis in Antirrhinum majus", The EMBO Journal, vol. 12, No. 10, pp. 3711–3719, 1993.
Koncz et al., "Isolation of a gene encoding a novel chloroplast protein by T–DNA tagging in Arabidopsis thaliana", The EMBO Journal, vol. 9, No. 5, pp. 1337–1346, 1990.
Papenbrock et al. "Mg–chelatase of tobacco: identification of Ch1 D cDNA sequence encoding a third subunit, analysis of the interaction of the three subunits with the yeast two–hybrid system, and reconstitution of the enzyme activity by co–expression of recombinant CHL D, CHL H and CHL 1", The Plant Journal, vol. 12, No. 5, pp. 981–990, Nov. 1997.
Papenbrock et al. "untitled" EMBL Sequence Data Library, Jan. 1, 1998.
Papenbrock et al. "Identification of a plant Ch1D cDNA sequence homologous to a bacterial gene encoding a third subunit of Mg–chelatase", EMBL Sequence Data Library, Jul. 1, 1997, Abstract No. XP002076481.
Luo et al., "Cloning and Sequencing of a cDNA Encoding the Putative Mg–Chelatase Subunit D (Accession No. AF014399) from Pea", Plant Physiology, vol. 115, No. 1 p. 315, Sep. 1997, Abstract No. XP002076482.
Kruse et al., "Isolation and characterisation of tobacco (Nicotiana tabacum) cDNA clones encoding proteins involved in magnesium chelation into protoporphyrin IX", Plant Molecular Biology, vol. 35, pp. 1053–1056, Dec. 1997.

* cited by examiner

*Primary Examiner*—James Ketter
(74) *Attorney, Agent, or Firm*—Frommer Lawrence & Haug LLP

(57) ABSTRACT

The present invention relates to a nucleic acid molecule which encodes a protein with the function of a plant Mg chelatase subunit CHLD or an active fragment thereof; a protein which has the function of a plant Mg chelatase subunit CHLD or an active fragment thereof, preferably a recombinant protein; a method of determining the interaction of plant Mg chelatase subunits, in which a host cell is transformed with a DNA sequence as claimed in one or more of claims 1 to 3 and at least with one DNA sequence encoding a further subunit of Mg chelatase in such a manner that the interaction of the Mg chelatase gene products leads to a directly or indirectly, qualitatively or quantitatively measurable signal, preferably by activating a marker gene, and transgenic plants, transgenic plant cells, transgenic plant organs, transgenic plant seeds, transgenic propagation material comprising an abovementioned nucleic acid molecule.

17 Claims, 2 Drawing Sheets

SEQUENCE LISTING

<160> NUMBER OF SEQ ID NOS: 17

<210> SEQ ID NO 1
<211> LENGTH: 2495
<212> TYPE: DNA
<213> ORGANISM: Nicotiana tabacum
<220> FEATURE:
<221> NAME/KEY: CDS
<222> LOCATION: (40)..(2313)
<223> OTHER INFORMATION: coding sequence for subunit chlD of plant magnesium chelatases

<400> SEQUENCE: 1

```
catctaaaat cctaaatcaa aaacttcgat gctataaaa atg ggg ttt tgt tca         54
                                          Met Gly Phe Cys Ser
                                          1               5 act tca acc ctc cca caa aca tca cta tcc aat tct caa tct tca aca        102
Thr Ser Thr Leu Pro Gln Thr Ser Leu Ser Asn Ser Gln Ser Ser Thr
            10                  15                  20 ttc ttc aca tac tta aaa cca tgc cca att cta tcc tcc aca tat tta       150
Phe Phe Thr Tyr Leu Lys Pro Cys Pro Ile Leu Ser Ser Thr Tyr Leu
        25                  30                  35 agg ccg gaa cgg cta aaa ttt cgc ctc aga ata agt gcc act gca act       198
Arg Pro Glu Arg Leu Lys Phe Arg Leu Arg Ile Ser Ala Thr Ala Thr
    40                  45                  50 att gat tca cct aat ggc gct gtt gca gta gtg gaa cct gaa aaa caa       246
Ile Asp Ser Pro Asn Gly Ala Val Ala Val Val Glu Pro Glu Lys Gln
55                  60                  65 cct gag aaa att tcc ttt ggt aga cag tat ttt cct cta gct gct gtt       294
Pro Glu Lys Ile Ser Phe Gly Arg Gln Tyr Phe Pro Leu Ala Ala Val
70                  75                  80                  85 att gga cag gat gct att aaa act gct ctt tta ctt ggg gcc att gac       342
Ile Gly Gln Asp Ala Ile Lys Thr Ala Leu Leu Leu Gly Ala Ile Asp
```

-continued

```
                   90                  95                 100
cgt gag ata gga gga att gca ata tgt ggg aag cgt gga aca gcg aaa        390
Arg Glu Ile Gly Gly Ile Ala Ile Cys Gly Lys Arg Gly Thr Ala Lys
            105                 110                 115 acg tta atg gca cgt gga ttg cat gct att ctg cca cca att gaa gta        438
Thr Leu Met Ala Arg Gly Leu His Ala Ile Leu Pro Pro Ile Glu Val
            120                 125                 130 gtt gtt ggc tca atg gca aat gct gat ccg aac tgt ccc gat gag tgg        486
Val Val Gly Ser Met Ala Asn Ala Asp Pro Asn Cys Pro Asp Glu Trp
            135                 140                 145 gaa gac ggg cta gct gac aga gca gaa tat ggg tct gat ggt aat atc        534
Glu Asp Gly Leu Ala Asp Arg Ala Glu Tyr Gly Ser Asp Gly Asn Ile
150                 155                 160                 165 aag acc cag ata gtt aaa tcc cca ttt gtt cag att ccc ctt ggt gtc        582
Lys Thr Gln Ile Val Lys Ser Pro Phe Val Gln Ile Pro Leu Gly Val
                170                 175                 180 aca gaa gat aga ttg att ggc tct gtt gat gtc gag gag tcc gtg aaa        630
Thr Glu Asp Arg Leu Ile Gly Ser Val Asp Val Glu Glu Ser Val Lys
                185                 190                 195 tct gga acc act gtc ttt caa cca ggc ctc ctc gca gaa gct cat cga        678
Ser Gly Thr Thr Val Phe Gln Pro Gly Leu Leu Ala Glu Ala His Arg
            200                 205                 210 gga gtt cta tat gtt gat gag att aat cta tta gat gaa ggt ata agt        726
Gly Val Leu Tyr Val Asp Glu Ile Asn Leu Leu Asp Glu Gly Ile Ser
            215                 220                 225 aac cta ctt ctg aat gta ttg act gag gga gtc aat att gta gaa aga        774
Asn Leu Leu Leu Asn Val Leu Thr Glu Gly Val Asn Ile Val Glu Arg
230                 235                 240                 245 gag gga atc agc ttt cga cat cca tgc aaa cca cta cta att gct acc        822
Glu Gly Ile Ser Phe Arg His Pro Cys Lys Pro Leu Leu Ile Ala Thr
                250                 255                 260 tat aac cct gaa gag ggt gcg gtt cgt gag cat ctg cta gac cgt att        870
Tyr Asn Pro Glu Glu Gly Ala Val Arg Glu His Leu Leu Asp Arg Ile
                265                 270                 275 gcg att aat tta agt gca gat ctt cca atg agt ttt gac gat cgt gtt        918
Ala Ile Asn Leu Ser Ala Asp Leu Pro Met Ser Phe Asp Asp Arg Val
            280                 285                 290 gca gct gtt gac ata gca aca cgt ttt cag gag tgt agc aat gag gtt        966
Ala Ala Val Asp Ile Ala Thr Arg Phe Gln Glu Cys Ser Asn Glu Val
            295                 300                 305 ttt aaa atg gtg gat gaa gaa aca gac agt gca aaa acc cag ata ata       1014
Phe Lys Met Val Asp Glu Glu Thr Asp Ser Ala Lys Thr Gln Ile Ile
310                 315                 320                 325 ttg gca agg gag tat tta aag gat gtc aca atc agt aga gat caa cta       1062
Leu Ala Arg Glu Tyr Leu Lys Asp Val Thr Ile Ser Arg Asp Gln Leu
                330                 335                 340 aaa tac ttg gtc atg gaa gca att cgt ggt ggc tgc cag ggg cac cga       1110
Lys Tyr Leu Val Met Glu Ala Ile Arg Gly Gly Cys Gln Gly His Arg
                345                 350                 355 gct gaa ctt tat gct gct cgt gta gcc aaa tgc tta gct gcc atc gat       1158
Ala Glu Leu Tyr Ala Ala Arg Val Ala Lys Cys Leu Ala Ala Ile Asp
            360                 365                 370 gga cgt gaa aaa gtt ggt gtt gat gag ctg aaa aaa gct gta gag ctt       1206
Gly Arg Glu Lys Val Gly Val Asp Glu Leu Lys Lys Ala Val Glu Leu
375                 380                 385 gtc atc ctc cca cgt tca act ata gtt gaa aac cca cca gac cag caa       1254
Val Ile Leu Pro Arg Ser Thr Ile Val Glu Asn Pro Pro Asp Gln Gln
390                 395                 400                 405 aac cag cag cca cct cct ccc cct ccc cct ccc caa aat caa gat tct       1302
```

```
                Asn Gln Gln Pro Pro Pro Pro Pro Pro Pro Gln Asn Gln Asp Ser
                                410             415             420 tca gaa gag cag aat gaa gaa gaa aaa gaa gaa gaa gat caa gag      1350
Ser Glu Glu Gln Asn Glu Glu Glu Lys Glu Glu Glu Asp Gln Glu
                425             430             435 gat gag aaa gat aga gaa aat gaa cag caa cag cca caa gtc cct gat  1398
Asp Glu Lys Asp Arg Glu Asn Glu Gln Gln Gln Pro Gln Val Pro Asp
            440             445             450 gag ttt att ttt gat gcg gaa ggt ggt tta gtg gat gaa aaa ctt ctc  1446
Glu Phe Ile Phe Asp Ala Glu Gly Gly Leu Val Asp Glu Lys Leu Leu
        455             460             465 ttc ttt gca caa caa gca caa aga cgc aaa gga aaa gct gga cga gca  1494
Phe Phe Ala Gln Gln Ala Gln Arg Arg Lys Gly Lys Ala Gly Arg Ala
470             475             480             485 aag aag gtc atc ttt tcc gaa gat aga ggt cga tat ata aag cca atg  1542
Lys Lys Val Ile Phe Ser Glu Asp Arg Gly Arg Tyr Ile Lys Pro Met
                490             495             500 ctt cca aag ggt cca gtg aag aga ttg gca gtt gat gca act cta aga  1590
Leu Pro Lys Gly Pro Val Lys Arg Leu Ala Val Asp Ala Thr Leu Arg
            505             510             515 gca gcg gca cca tat cag aag tta cga aga gca aag gac atc caa aaa  1638
Ala Ala Ala Pro Tyr Gln Lys Leu Arg Arg Ala Lys Asp Ile Gln Lys
        520             525             530 act cgc aag gtt tat gta gag aaa act gac atg aga gcc aaa aga atg  1686
Thr Arg Lys Val Tyr Val Glu Lys Thr Asp Met Arg Ala Lys Arg Met
535             540             545 gca cgc aaa gcc gga gct ctg gtg ata ttc gta gtt gac gct agt ggg  1734
Ala Arg Lys Ala Gly Ala Leu Val Ile Phe Val Val Asp Ala Ser Gly
550             555             560             565 agt atg gca ctg aat aga atg cag aat gcc aaa gga gca gca ctt aaa  1782
Ser Met Ala Leu Asn Arg Met Gln Asn Ala Lys Gly Ala Ala Leu Lys
                570             575             580 cta ctt gca gag agt tat aca agc aga gat cag gtc tgt atc att ccc  1830
Leu Leu Ala Glu Ser Tyr Thr Ser Arg Asp Gln Val Cys Ile Ile Pro
            585             590             595 ttc cgc gga gat gct gct gaa gtt ttg ttg cca cct tct agg tca ata  1878
Phe Arg Gly Asp Ala Ala Glu Val Leu Leu Pro Pro Ser Arg Ser Ile
        600             605             610 tcg atg gca aga aat cgt ctt gag aga ctt ccc tgt gga ggg ggt tct  1926
Ser Met Ala Arg Asn Arg Leu Glu Arg Leu Pro Cys Gly Gly Gly Ser
615             620             625 ccc ctt gct cat ggg ctt acg acg gca gtt aga gtt gga atg aat gca  1974
Pro Leu Ala His Gly Leu Thr Thr Ala Val Arg Val Gly Met Asn Ala
630             635             640             645 gaa aag agt ggt gat gtt gga cgt atc atg att gtt gca att act gat  2022
Glu Lys Ser Gly Asp Val Gly Arg Ile Met Ile Val Ala Ile Thr Asp
                650             655             660 ggt aga gct aac atc tct ctt aaa aga tcc aca gac cct gaa gct gaa  2070
Gly Arg Ala Asn Ile Ser Leu Lys Arg Ser Thr Asp Pro Glu Ala Glu
            665             670             675 gct tct gat gca ccc aga cct tct tcc caa gag ctg aag gat gag att  2118
Ala Ser Asp Ala Pro Arg Pro Ser Ser Gln Glu Leu Lys Asp Glu Ile
        680             685             690 ctc gag gtg gct ggt aaa ata tac aaa aca gga atg tct ctc ctc gtc  2166
Leu Glu Val Ala Gly Lys Ile Tyr Lys Thr Gly Met Ser Leu Leu Val
695             700             705 ata gat aca gaa aat aag ttt gtt tct act ggt ttt gcg aaa gaa atc  2214
Ile Asp Thr Glu Asn Lys Phe Val Ser Thr Gly Phe Ala Lys Glu Ile
710             715             720             725
```

-continued

```
gcg aga gta gct caa ggg aag tac tat tat tta cca aat gct tca gat    2262
Ala Arg Val Ala Gln Gly Lys Tyr Tyr Tyr Leu Pro Asn Ala Ser Asp
            730                 735                 740 gct gtg ata tct gca aca aag gat gca tta tct gca tta aag gaa        2310
Ala Val Ile Ser Ala Thr Lys Asp Ala Leu Ser Ala Leu Lys Glu
        745                 750                 755 tct tgacctaaac tcgatcgaat taattgtaaa tgttgttttg agtatagatt         2363
Ser attgggagga tataagagct tgcttgataa ttcttatctt ttgttgtact aattgaactt  2423
atttctcaat tatgcaatca gggtaatgaa gattcttttc atttcaaaaa aaaaaaaaa   2483 aaaggaattc ga                                                      2495
```

<210> SEQ ID NO 2
<211> LENGTH: 758
<212> TYPE: PRT
<213> ORGANISM: Nicotiana tabacum

<400> SEQUENCE: 2

```
Met Gly Phe Cys Ser Thr Ser Thr Leu Pro Gln Thr Ser Leu Ser Asn
1               5                   10                  15

Ser Gln Ser Ser Thr Phe Phe Thr Tyr Leu Lys Pro Cys Pro Ile Leu
            20                  25                  30

Ser Ser Thr Tyr Leu Arg Pro Glu Arg Leu Lys Phe Arg Leu Arg Ile
        35                  40                  45

Ser Ala Thr Ala Thr Ile Asp Ser Pro Asn Gly Ala Val Ala Val Val
    50                  55                  60

Glu Pro Glu Lys Gln Pro Glu Lys Ile Ser Phe Gly Arg Gln Tyr Phe
65                  70                  75                  80

Pro Leu Ala Ala Val Ile Gly Gln Asp Ala Ile Lys Thr Ala Leu Leu
                85                  90                  95

Leu Gly Ala Ile Asp Arg Glu Ile Gly Gly Ile Ala Ile Cys Gly Lys
            100                 105                 110

Arg Gly Thr Ala Lys Thr Leu Met Ala Arg Gly Leu His Ala Ile Leu
        115                 120                 125

Pro Pro Ile Glu Val Val Gly Ser Met Ala Asn Ala Asp Pro Asn
    130                 135                 140

Cys Pro Asp Glu Trp Asp Gly Leu Ala Asp Arg Ala Glu Tyr Gly
145                 150                 155                 160

Ser Asp Gly Asn Ile Lys Thr Gln Ile Val Lys Ser Pro Phe Val Gln
                165                 170                 175

Ile Pro Leu Gly Val Thr Glu Asp Arg Leu Ile Gly Ser Val Asp Val
            180                 185                 190

Glu Glu Ser Val Lys Ser Gly Thr Thr Val Phe Gln Pro Gly Leu Leu
        195                 200                 205

Ala Glu Ala His Arg Gly Val Leu Tyr Val Asp Glu Ile Asn Leu Leu
    210                 215                 220

Asp Glu Gly Ile Ser Asn Leu Leu Leu Asn Val Leu Thr Glu Gly Val
225                 230                 235                 240

Asn Ile Val Glu Arg Glu Gly Ile Ser Phe Arg His Pro Cys Lys Pro
                245                 250                 255

Leu Leu Ile Ala Thr Tyr Asn Pro Glu Glu Gly Ala Val Arg Glu His
            260                 265                 270

Leu Leu Asp Arg Ile Ala Ile Asn Leu Ser Ala Asp Leu Pro Met Ser
        275                 280                 285
```

```
Phe Asp Asp Arg Val Ala Ala Val Asp Ile Ala Thr Arg Phe Gln Glu
    290                 295                 300

Cys Ser Asn Glu Val Phe Lys Met Val Asp Glu Thr Asp Ser Ala
305                 310                 315                 320

Lys Thr Gln Ile Ile Leu Ala Arg Glu Tyr Leu Lys Asp Val Thr Ile
                325                 330                 335

Ser Arg Asp Gln Leu Lys Tyr Leu Val Met Glu Ala Ile Arg Gly Gly
            340                 345                 350

Cys Gln Gly His Arg Ala Glu Leu Tyr Ala Ala Arg Val Ala Lys Cys
        355                 360                 365

Leu Ala Ala Ile Asp Gly Arg Glu Lys Val Gly Val Asp Glu Leu Lys
    370                 375                 380

Lys Ala Val Glu Leu Val Ile Leu Pro Arg Ser Thr Ile Val Glu Asn
385                 390                 395                 400

Pro Pro Asp Gln Gln Asn Gln Gln Pro Pro Pro Pro Pro Pro Pro Pro
                405                 410                 415

Gln Asn Gln Asp Ser Ser Glu Glu Gln Asn Glu Glu Glu Glu Lys Glu
            420                 425                 430

Glu Glu Asp Gln Glu Asp Glu Lys Asp Arg Glu Asn Glu Gln Gln Gln
        435                 440                 445

Pro Gln Val Pro Asp Glu Phe Ile Phe Asp Ala Glu Gly Gly Leu Val
    450                 455                 460

Asp Glu Lys Leu Leu Phe Phe Ala Gln Ala Gln Arg Arg Lys Gly
465                 470                 475                 480

Lys Ala Gly Arg Ala Lys Lys Val Ile Phe Ser Glu Asp Arg Gly Arg
                485                 490                 495

Tyr Ile Lys Pro Met Leu Pro Lys Gly Pro Val Lys Arg Leu Ala Val
            500                 505                 510

Asp Ala Thr Leu Arg Ala Ala Pro Tyr Gln Lys Leu Arg Arg Ala
        515                 520                 525

Lys Asp Ile Gln Lys Thr Arg Lys Val Tyr Val Glu Lys Thr Asp Met
    530                 535                 540

Arg Ala Lys Arg Met Ala Arg Lys Ala Gly Ala Leu Val Ile Phe Val
545                 550                 555                 560

Val Asp Ala Ser Gly Ser Met Ala Leu Asn Arg Met Gln Asn Ala Lys
                565                 570                 575

Gly Ala Ala Leu Lys Leu Leu Ala Glu Ser Tyr Thr Ser Arg Asp Gln
            580                 585                 590

Val Cys Ile Ile Pro Phe Arg Gly Asp Ala Ala Glu Val Leu Leu Pro
        595                 600                 605

Pro Ser Arg Ser Ile Ser Met Ala Arg Asn Arg Leu Glu Arg Leu Pro
    610                 615                 620

Cys Gly Gly Gly Ser Pro Leu Ala His Gly Leu Thr Thr Ala Val Arg
625                 630                 635                 640

Val Gly Met Asn Ala Glu Lys Ser Gly Asp Val Gly Arg Ile Met Ile
                645                 650                 655

Val Ala Ile Thr Asp Gly Arg Ala Asn Ile Ser Leu Lys Arg Ser Thr
            660                 665                 670

Asp Pro Glu Ala Glu Ala Ser Asp Ala Pro Arg Pro Ser Ser Gln Glu
        675                 680                 685

Leu Lys Asp Glu Ile Leu Glu Val Ala Gly Lys Ile Tyr Lys Thr Gly
    690                 695                 700

Met Ser Leu Leu Val Ile Asp Thr Glu Asn Lys Phe Val Ser Thr Gly
```

```
                   705                 710                 715                 720
        Phe Ala Lys Glu Ile Ala Arg Val Ala Gln Gly Lys Tyr Tyr Tyr Leu
                        725                 730                 735

Pro Asn Ala Ser Asp Ala Val Ile Ser Ala Ala Thr Lys Asp Ala Leu
                    740                 745                 750

Ser Ala Leu Lys Glu Ser
                755

<210> SEQ ID NO 3
<211> LENGTH: 6
<212> TYPE: PRT
<213> ORGANISM: Synechocystis PCC6803
<220> FEATURE:
<221> NAME/KEY: PEPTIDE
<222> LOCATION: (1)..(6)
<223> OTHER INFORMATION: peptide sequence derived from chlD gene of
      synechocystis PCC6803

<400> SEQUENCE: 3

Val Asp Ala Ser Gly Ser
1               5

<210> SEQ ID NO 4
<211> LENGTH: 6
<212> TYPE: PRT
<213> ORGANISM: Synechocystis PCC6803
<220> FEATURE:
<221> NAME/KEY: PEPTIDE
<222> LOCATION: (1)..(6)
<223> OTHER INFORMATION: peptide sequence derived from chlD gene of
      synechocystis PCC6803

<400> SEQUENCE: 4

Thr Asp Gly Arg Gly Asn
1               5

<210> SEQ ID NO 5
<211> LENGTH: 1579
<212> TYPE: DNA
<213> ORGANISM: Nicotiana tabacum
<220> FEATURE:
<221> NAME/KEY: misc_feature
<222> LOCATION: (1)..(1579)
<223> OTHER INFORMATION: coding sequence for subunit chlI of plant
      magnesium chelatases

<400> SEQUENCE: 5
cccaaaattc ttcttcttct tcttcactga aaaattctaa acaaaatggc ttcactacta      60
ggaacttcct cttcagcagc agctgcaata ttagcttcta cacccttgtc ttctcgctcc    120
tgtaagcctg ccgttttctc cctcttccct tcttcagggc agagtcaagg gaggaagttt    180
tatggaggga ttagagtccc agttaagaaa gggaggtccc aattccatgt ggcaatttca    240
aatgttgcga cggaaatcaa cctgctcaag acagggtca gaaacttgct ggaggagagc     300
cagagaccgg tgtatccatt tgcagctata gtgggacaag atgaaatgaa gttatgtctt    360
ttgctgaatg taattgatcc aaagattgga ggtgtgatga taatgggtga taggggaacc    420
gggaagtcca ccacggttag atctttggta gatttacttc ctgaaatcaa agttatttct    480
ggtgatccgt tcaattcaga tccagatgac caagaagtaa tgagtgcaga agtccgtgac    540 aaaattgagga gcggacagca gcttcctata tctcgtacga aaatcaacat ggttgattta    600
ccgcttggtg ctactgagga cagggtgtgt ggcacaatcg acattgagaa agctcttact    660
gagggtgtga aggctttcga gcctggtctt cttgctaaag ctaacagagg aatactttac    720
```

-continued

```
gtcgatgagg ttaatctttt ggacgaccat ttagtagatg ttcttttgga ttctgcagca    780
tcgggatgga acactgttga agagagggg atatcaatat cacaccctgc ccggtttatc    840
cttattggtt cgggtaatcc tgaagaagga gaacttaggc cacaacttct tgatcgattt    900
ggaatgcatg cccaagtggg gaccgtgaga gatgcagagc tgagagtgaa gatagttgag    960
gaaagagctc gttttgataa aaccccaag gaattcaggg aatcatacaa ggcagagcaa   1020
gaaaagctcc agaaccaaat cgactcagct aggaacgctc tttctgctgt acaatcgat   1080
catgatcttc gagttaaaat ctctaaggtc tgtgcagaac taaacgtcga tggattgaga   1140
ggtgatatag tcactaacag ggcagcaaga gcgttggctg cactaaaagg aagagataag   1200
gtaactccgg aagatatcgc cactgtcatt cccaactgct taagcacag gctgaggaag   1260
gatccgttgg aatctattga ctcgggtgta cttgttgttg agaaatttta tgaggttttc   1320
gcctaagcgt tttatagagt gagatactta tttttggctt tattttccat tcataaatca   1380
tctaaagatt tgacaattgt aacactagac ttttgcttaa ttttggcttt gtactgtgct   1440
taagaaatgg gttcagaatt acctgtagcc agttgtattt ggttatgact gctttatttc   1500
tgaaatgctt aaaaaaaaaa aaaaaaaaaa aaaaaaaaaa aaaaaaaaaa aaaaaaaaaa   1560
aaaaaaaaaa aaggaattc                                                1579
```

```
<210> SEQ ID NO 6
<211> LENGTH: 4578
<212> TYPE: DNA
<213> ORGANISM: Nicotiana tabacum
<220> FEATURE:
<221> NAME/KEY: misc_feature
<222> LOCATION: (1)..(4578)
<223> OTHER INFORMATION: sequence for subunit chlH of plant magnesium
      chelatases

<400> SEQUENCE: 6
```

```
agccactact ctccacataa aactataaac ttagaacatt tcacttgaaa aagagagga     60
aaaaagtgaa gcagaaatct tttctcaaaa cacaatctat aggaagttaa attcaacttc    120
cacacttcca agattcttgt ttcaagtttc gtttagtttt ttttttcttgg tttttttttat    180
agttttctgt acaattttgt gtagaatcaa gaaacgaaag agttaaagtt tgaaactttt    240
ttacaagttt gaaacaatgg cttctttggt ttcttcacca tttacattgc caaattcaaa    300
agtagaacac ttgtcatcca tttctcaaaa gcattacttt cttcactcat ttcttcccaa    360
gaaaataaac cccacttact caaaatcacc aaagaaattc caatgtaatg ctattggcaa    420
tggtttattc actcaaacaa ctcaagaagt taggagaatt gtgcctgaaa atactcaggg    480
acttgctact gtgaaaatag tctatgttgt attggaagct cagtaccaat catcacttac    540
tgctgctgtt cagacactga acaagaatgg tcagtttgct tcttttgagg ttgtggggta    600
cttggttgag gagcttagag atgagaatac ttataaaatg ttttgtaaag atcttgagga    660
tgcaaatgtg tttattggtt cattgatttt tgtggaagaa ttggctttaa aggtaaaatc    720
tgcagtggag aaagaaaggg acagacttga tgcagttttg gtgtttccat caatgcctga    780
ggtgatgagg ttgaacaagt tgggatcttt tagtatgtca caattggggc aatcaaagag    840
tccatttttt gagcttttca agaagaagaa accttcttct gcaggttttt ctgatcagat    900
gttgaagctt gtgagaacat tgcctaaggt tttgaagtat ttaccaagtg ataaagctca    960
agatgctagg ttgtacatac taagtttgca gttttggcta ggaggttcac ctgataattt   1020
ggtgaatttc ttgaaaatga tttctggttc ttatgttcct gctcttaaag ggatgaaaat   1080
```

-continued

```
cgactactcg gatccggttt tgtacttgga taatggaatt tggcaccctt tggctccttg    1140
tatgtatgat gatgtgaagg agtatttgaa ttggtatgca acaaggagag atactaatga    1200
gaaactcaag agttcaaatg ctcctgttgt tgggctggtt ttgcaaagga gtcatattgt    1260
tacttgtgat gagagtcact atgtggctgt gatcatggaa ttggaggcaa aggggctaa     1320 agttatccca atttttgccg gtgggctaga cttttcgagg ccaattgaga gatatttcat    1380
tgatcctatt acaaagaagc cttttgtgaa ttcagtaata tcactttctg gttttgcact    1440
tgttggaggg ccagcaagac aagaccatcc aagggcaata gaggctttga tgaaacttga    1500
tgtgccttat attgtggcat tgcctttggt tttccaaaca acagaggaat ggttgaacag    1560
tactttgggg ctgcacccta ttcaggtggc tctacaagtt gctctccctg agctggatgg    1620
aggaatggag cccatcgtat tcgccggtcg cgatccaaga acagggaaat cacatgctct    1680
tcacaaaaga gtggagcagc tttgcaccag ggcaatcaaa tggggagagt aaagagaaa     1740 aacaaaggct gagaagaggt tggcaatcac tgtcttcagc tttcctccag acaaaggcaa    1800
tgtcggaact gctgcatact tgaatgtctt tgcctccata tactctgttc tcaaagatct    1860
caagaaagac ggctacaacg ttgaggggct gcctgagact tctgcacaac ttattgaaga    1920
agtaattcac gacaaagaag ctcagttcag cagcccaaat cttaacatag cttacaagat    1980
gaatgttaga gaataccaga agctaacccc ctatgctact gctcttgaag aaaactgggg    2040
gaaagcacct ggtaatttga actctgatgg agaaaacctc ttggtatatg gtaaacagta    2100
cggcaatgtc tttatcggtg ttcagcccac gtttggatac gagggtgacc cgatgagact    2160
tctgttctcc aaatcagcta gccctcacca tggttttgct gcatactatt cctttgtgga    2220
gaaaattttc aaagctgatg cagttctcca cttttggtact catggttctc ttgagttcat    2280
gccaggtaaa caggtgggaa tgagcgatgc ttctttccct gatagtctca ttggaaacat    2340
tcccaatgtc tattactatg cagcaaacaa cccatctgaa gcaactattg ccaaacgaag    2400
gagttatgcg aataccatta gctacttgac tcctccggct gagaatgctg gactctacaa    2460
gggactcaag cagctcagtg agctcatttc ctcataccaa tctctgaaag actcaggccg    2520
tggccaacag attgtgaact ctatcatcag tacagctaga cagtgtaatc ttgacaagga    2580
tgttgatctt ccagaagaag gggaggaaat ctcggccaaa gagcgtgacc ttgtggtagg    2640
aaaagtatac tctaagatta tggagatcga gtctcgtctt cttccgtgtg gacttcacat    2700
cattggtgaa cctccaaccg cgatggaagc agttgctact cttgtcaata ttgcgacatt    2760
ggaccgtcct gaagagggta tttctgccct tccatctata ttggctgcga cggttggaag    2820
aagcattgag gagatttaca gaggcaatga ccagggcatc ttacgagatg tggagctgct    2880
ccgtcaaatt actgaggcat cacgtggagc aatatcagca tttgttgaac gtacgacaaa    2940
caacaagggt caggttgtga atgtcaatga caagctaacc tcaatccttg gttttggtat    3000
aaatgaacca tggatccagt atttgtcaaa cacccaattt tacagagctg ataggggacaa   3060 gctcagagtt ctattccagt tcttgggaga gtgtctgaag ctaattgtcg ctaacaacga    3120
ggtgggaagc ttgaaacagg ctctagaagg gaaatatgtt gaaccaggtc caggagggga    3180
tccgatcaga aacccgaaag ttttgcctac tgggaaaaac atccatgctt tggacccaca    3240
agctattccc acaatagcag cagtgcagag tgccaaaatt gttgttgaaa gattgttgga    3300
gaggcaaaag gccgacaacg ggggcaagta cccggagact gttgctctgg ttctttgggg    3360
aacagacaac atcaagacct atggagagtc attggcacag gttatgtgga tgattggtgt    3420
```

-continued

```
taggccagtt acagactcgt taggacgggt taaccgggtg gaacctgtta gccttgaaga    3480
gcttggaagg cctagagttg atgttgttgt caactgctct ggggtgttca gagatctctt    3540
catcaatcag atgaatctcc ttgaccgagc agtcaagatg gttgcagagc tcgacgagcc    3600
agaagaccaa aactacgtca ggaaacatgc actagaacaa gcaaaaacac tcggagttga    3660
tgttcgtgaa gctgctacaa ggatcttctc aaatgcttca ggatcttact cctccaacat    3720
taaccttgct gttgagaatt caacatgaaa tgatgagaag caacttcaag acatgtactt    3780
gagccgaaag tcatttgcat ttgactgtga tgcccctggt gttggcatga ctgagaagag    3840
gaaagttttt gagatggctc ttagcacggc tgatgccaca ttccagaacc ttgactcatc    3900
tgaaatttca ttcacagacg tgagtcacta cttcgattca gacccaacca accttgtgca    3960
aaacctcagg aaagacggga agaagcctag tgcatacatt gctgacacca ctactgctaa    4020
tgctcaggta cgtacgttgt ctgagactgt gaggcttgac gcaaggacaa agttgttgaa    4080
ccccaagtgg tatgaaggca tgctatccac tggctacgag ggtgttcgtg agattgagaa    4140
acgattaact aacacagtgg ggtggagtgc aacttcaggc caagttgata attgggtgga    4200
tgaagaagcc aacacaacct tcattcaaga tcaggagatg ttgaacaggc tcatgaacac    4260
aaatccaaat tctttcagga agttgcttca gacattcttg gaagccaacg ggcgtggata    4320
ctgggaaact tctgcagaga acattgagaa actcaagcaa ttatactcag aagttgaaga    4380
caagattgag ggaatcgatc gataaatgta tagcaaaaag aatgatctct gattattgcc    4440
tgtttgttcc taactgtttc tgatgtgaat tcctttgaca gtccccagtg taattttgtt    4500 cattttggg gatgtcctac ttctatgaga aaatactgct tccatatatt caaatttgag    4560
cttgaaaaaa aaaaaaaa                                                 4578
```

<210> SEQ ID NO 7
<211> LENGTH: 6
<212> TYPE: PRT
<213> ORGANISM: Synechocystis PCC6803
<220> FEATURE:
<221> NAME/KEY: PEPTIDE
<222> LOCATION: (1)..(6)
<223> OTHER INFORMATION: peptide sequence derived from chlD gene of
      synechocystis PCC6803

<400> SEQUENCE: 7

Ala Lys Gly Ala Val Met
1               5

<210> SEQ ID NO 8
<211> LENGTH: 18
<212> TYPE: DNA
<213> ORGANISM: Artificial
<220> FEATURE:
<223> OTHER INFORMATION: PCR primer
<221> NAME/KEY: variation
<222> LOCATION: (1)..(16)
<223> OTHER INFORMATION: nucleotide 'n' can be any nucleotide 'a', 'c',
      'g' or 't', nucleotide 'y' can be either nucleotide 'c' or 't',
      nucleotide 'r' can be either nucleotide 'a' or 'g',
      nucleotide 'w' can be either nucleotide 'a' or 't'.

<400> SEQUENCE: 8
gaygtngara arwcngtn                                                  18

<210> SEQ ID NO 9
<211> LENGTH: 19
<212> TYPE: DNA
<213> ORGANISM: Artificial

```
<220> FEATURE:
<223> OTHER INFORMATION: PCR primer
<221> NAME/KEY: variation
<222> LOCATION: (1)..(19)
<223> OTHER INFORMATION: nucleotide 'n' can be any nucleotide 'a', 'c',
      'g' or 't' and nucleotide 'r' can be either nucleotide 'a' or 'g'.

<400> SEQUENCE: 9
atrttnccnc gnccrtcng                                                    19

<210> SEQ ID NO 10
<211> LENGTH: 19
<212> TYPE: DNA
<213> ORGANISM: Artificial
<220> FEATURE:
<223> OTHER INFORMATION: PCR primer
<221> NAME/KEY: variation
<222> LOCATION: (1)..(19)
<223> OTHER INFORMATION: nucleotide 'n' can be any nucleotide 'a', 'c',
      'g' or 't' and nucleotide 'r' can be either nucleotide 'a' or 'g'

<400> SEQUENCE: 10
gcnaarggng cngtnatgc                                                    19

<210> SEQ ID NO 11
<211> LENGTH: 33
<212> TYPE: DNA
<213> ORGANISM: Artificial
<220> FEATURE:
<223> OTHER INFORMATION: Primer

<400> SEQUENCE: 11
tgacccgggg gtagtggaac ctgaaaaaca acc                                    33

<210> SEQ ID NO 12
<211> LENGTH: 33
<212> TYPE: DNA
<213> ORGANISM: Artificial
<220> FEATURE:
<223> OTHER INFORMATION: Primer

<400> SEQUENCE: 12
ggcgaattct caagattcct ttaatgcaga taa                                    33

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
gcggtcgact caagattcct ttaatgcaga                                        30

<210> SEQ ID NO 14
<211> LENGTH: 33
<212> TYPE: DNA
<213> ORGANISM: Artificial
<220> FEATURE:
<223> OTHER INFORMATION: Primer

<400> SEQUENCE: 14
gctgatatcg gctattggca atggtttatt cac                                    33

<210> SEQ ID NO 15
<211> LENGTH: 30
<212> TYPE: DNA
```

```
-continued

<213> ORGANISM: Artificial
<220> FEATURE:
<223> OTHER INFORMATION: Primer

<400> SEQUENCE: 15
gcgtcgacat ttatcgatcg attccctcaa                              30

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
cagcccgggt ccactactag g                                       21

<210> SEQ ID NO 17
<211> LENGTH: 24
<212> TYPE: DNA
<213> ORGANISM: Artificial
<220> FEATURE:
<223> OTHER INFORMATION: Primer

<400> SEQUENCE: 17
caggtcgagg cacagtacaa agcc                                    24
```

DNA SEQUENCES ENCODING FOR SUBUNIT CHLD OF PLANT MAGNESIUM CHELATASES AND DETERMINING THE ACTIVITY OF PLANT MAGNESIUM CHELATASES

CROSS-REFERENCE TO RELATED APPLICATIONS

This application claims priority from International Application No. PCT/EP98/02483, filed Apr. 27, 1998 and German Application No. 197 17 656.9, filed Apr. 25, 1997. Each of the foregoing applications, patents and publications and all documents cited or referenced therein ("application cited documents") and all documents cited or referenced in this specification ("herein cited documents") are hereby incorporated herein by reference.

STATEMENT REGARDING FEDERALLY SPONSORED RESEARCH

Not applicable.

FIELD OF THE INVENTION

The present invention relates to the subunit CHLD of plant magnesium chelatase (Mg chelatase), to DNA sequences encoding the subunit CHLD of plant Mg chelatase, to processes for preparing the subunit CHLD of plant Mg chelatase, to processes for determining the activity of plant Mg chelatase, and transgenic plants which have been transformed with the Mg chelatase DNA according to the invention.

BACKGROUND OF THE INVENTION

Being photosystem cofactors, chlorophylls play a role in the conversion of light into chemical energy and are thus required for plant growth and survival.

Magnesium is incorporated into porphyrin during chlorophyll biosynthesis with the aid of a membrane—associated enzyme, namely Mg chelatase, which is composed of several subunits.

It has already been disclosed that bacterial Mg chelatase is composed of three subunits (D, H and I), whose corresponding gene sequences are termed bchD, bchH and bchI (Burke et al. (1993), J. Bacteriol. 175, 2414–2422; Coomber et al. (1990), Mol. Microbiol. 4, 977–989; Gibson et al. (1995), Proc. Natl. Acad. Sci. USA, 92, 1941–1844; Jensen et al. (1996), J. Biol. Chem. 271, 16662–16667).

TABLE I

List of the genes of known Mg chelatase subunits

| Rhodobacter capsulatus | Rhodobacter sphaeroides | Synechocystis PCC 6803 | Arabidopsis thaliana | Antirrhinum majus |
|---|---|---|---|---|
| Burke et al. | Coomber et al. | Jensen et al. | Koncz et al. | Hudson et al. |
| bchD | bchD | chlD | | |
| bchH | bchH | chlH | chiH | olive |
| bchI | bchI | chlI | ch42 | 3Dchl |

As regards plant Mg chelatases, two subunits have been described to date which seem to correspond to the bacterial Mg chelatase subunits bchH and bchI (Koncz et al., (1990), EMBO J. 9, 1337–1346; Hudson et al., (1993), EMBO J. 12, 3711–3719; Eibson et al., (1996), Plant Physiol. 121, 61–71). It is not known as yet which other subunits participate in the structure of plant Mg chelatase. No enzyme activity was observed with the two known plant subunits CHLI and CHLH, neither alone nor together with the known bacterial subunits of type D (CHLD and BCHD).

Due to their key position in chlorophyll biosynthesis, plant Mg chelatase is a radically new starting point for developing a novel generation of herbicidal compounds with highly specific activity. In addition, the vitality and/or growth of phototrophic uni- and multicellular organisms, in particular bacteria, algae and plants, can be controlled to a high degree by influencing gene expression (suppression, overexpression) of the natural or modified (for example genetically engineered) expression products of Mg chelatase or else by specific Mg chelatase inhibitors.

The enzymatic activity of plant Mg chelatase was originally measured on intact chloroplasts (Castelfranco et al., (1979) Arch. Biochem. Biophys. 192, 592–598; Fuesler et al. (1982) Plant Physiol. 69,421–423). Since then, the activity was also determined on disrupted plastids (Walker et al. (1991) Proc. Natl. Acad. Sci. 88, 5789–5793) and subplastid membrane fractions (Lee, et al. (1992). Plant Physiol. 99,1134–1140).

Surprisingly, there has now been found a DNA which encodes a subunit of the enzyme plant Mg chelatase. The DNA will subsequently be termed chlD, and the amino acid sequence CHLD.

Moreover, it has been found that a subunit CHLD of plant Mg chelatase together with the subunits CHLI and CHLH is, surprisingly, suitable for reconstituting a funtionally intact, i.e. enzymatically active, plant Mg chelatase, so that the plant Mg chelatase subunit CHLD according to the invention provides novel test methods (in vivo and in vitro) for plant Mg chelatase activity.

DETAILED DESCRIPTION OF THE INVENTION

Figure 1A:
FIGS. 1A–1D depict transgenic antisense and sense CHLD tobacco plants.

The present invention therefore relates to a nucleic acid molecule which encodes a protein with the function of a plant Mg chelatase subunit CHLD, preferably a nucleic acid molecule as shown in SEQ ID NO: 1, a biologically active fragment thereof, and complementary or antisense sequences.

The invention relates to plant chlD sequences, preferably from dicotyledonous plants, especially preferably Solanaceae and, in particular, Nicotiana tabacum.

The present invention futhermore relates to a nucleic acid molecule which encodes a protein in accordance with SEQ ID NO: 2 with the function of a plant Mg chelatase subunit CHLD or a biologically active fragment thereof or it forms a complementary or antisense sequence to such a nucleic acid molecule.

A further object of the present invention is a nucleic acid molecule which is an oligonucleotide of at least 10 nucleotides in length and which hybridizes specifically with a nucleic acid molecule which encodes a protein with the function of a plant Mg chelatase subunit CHLD, preferably SEQ ID NO: 1, a fragment thereof or its complementary or antisense sequences.

The term "to hybridize specifically" is generally understood to refer to the characteristic of a single-stranded nucleic acid molecule to form, together with a complementary nucleic acid molecule, hydrogen bridges, base pairs and, if appropriate, a double strand.

Another object of the present invention is a nucleic acid molecule which encodes a peptide from the group consisting of SEQ ID NO: 3, SEQ ID NO: and SEQ ID NO: 7, and their complementary or antisense sequences.

The term "recombinant organism" is to be understood as meaning the cell of an organism which has been modified by altering its DNA in vitro or by integration of DNA, for example recombinant yeast, bacterial, algal, insect or plant cells.

Writing "chI" in small letters is conventionally used for the genes of Mg chelatase subunits D, I and H, while the capitalization "CHL" refers to the gene products, i.e. proteins.

A further object of the present invention is the use of the nucleic acid molecules according to the invention for amplifying, isolating or identifying a nucleic acid molecule encoding a protein with the function of a plant Mg chelatase subunit CHLD or a biologically active fragment thereof, in particular of chlD structural genes or chlD mRNA of other organisms, preferably of plant or microbial origin.

The invention furthermore also relates to the use of the nucleic acid molecules according to the invention for raising antibodies against their expression products.

Another object of the invention are non-naturally occurring chimeric genes comprising a promoter which is functionally fused to a DNA molecule according to the invention.

Another object of the invention is a vector, preferably a recombinant vector, comprising a nucleic acid molecule according to the invention comprising a chimeric gene comprising a promoter, which is functionally fused to a DNA molecule according to the invention.

Another object of the invention is a recombinant host cell which expresses a DNA molecule according to the invention, this host cell preferably being stably transformed with a recombinant vector comprising a chimeric gene comprising a promoter which is functionally fused to a nucleic acid molecule according to the invention or which is transformed by other transformation methods known to those skilled in the art and expresses a DNA molecule according to the invention.

The invention furthermore relates to the use of the nucleic acid molecules according to the invention for generating transgenic plants.

Another object of the invention are transgenic plants, transgenic plant cells, transgenic plant organs, transgenic plant seeds, transgenic propagation material comprising a nucleic acid molecule according to the invention.

Another object of the invention are methods of generating transgenic plants, transgenic plant cells, transgenic plant organs, transgenic plant seeds, transgenic propagation material by means of recombinant host cell, wherein this host cell is transformed with a DNA molecule according to the invention.

The invention also relates to propagation material of the plants according to the invention, for example fruits, seeds, tubers, root stocks, seedlings and cuttings.

Suitable excipient plants for a gene according to the invention are all agriculturally important monocotyledonous and dicotyledonous crop plants, preferably maize and other cereals such as, for example, wheat, rye, barley, panic grasses, oats, cassava and rice, and also cotton, tobacco, sugar beet, sugar cane, potatoes, oilseed rape, sunflowers, soya, or fruit and vegetable species.

To express the nucleic acid molecules according to the invention in plant cells, they are linked to regulatory DNA elements which ensure transcription in plant cells. These include, in particular, promoters. In general, any promoter which is active in plant cells is suitable for expression.

The promoter may be chosen in such a way that expression is constitutive or only takes place in a certain tissue, at a certain point in time of the plant's development or at a point in time determined by external factors. As regards the plant, the promoter can be homologous or heterologous. Examples of suitable promoters are the cauliflower mosaic virus 35S RNA promoter and the maize ubiquitin promoter for constitutive expression, the patatin gene promoter B35 (Rocha-Sosa et al., EMBO J. 8 (1989), 23–29) for sink-specific expression (for example potato tubers, beet, tomato fruit) or a promoter which ensures expression only in photosynthetically active tissues, for example the ST-LS1 promoter (Stockhaus et al., Proc. Natl. Acad. Sci. USA 84 (1987), 7943–7947; Stockhaus et al., EMBO J. 8 (1989), 2445–2451), all promoters which are constitutively active in plastids, for example the psbA cassette expression signal sequences (Staub & Maliga (1993) EMBO Journal 12: 601–606; Zoubenko et al. (1994) Nucleic Acids Research 22: 3819–3824) and the Prn promoter (Svab+Maliga (1993) Proc. Natl. Acad. Sci. USA 90:913–917) or, for endosperm-specific expression, the wheat HMG promoter, the USP promoter, the phaseolin promoter, or promoters from maize zein genes. Furthermore, a termination sequence may be present which serves for correctly terminating transcription and for adding a poly-A tail to the transcript, which is assumed to have a function in stabilizing the transcripts. Such elements are described in the literature (cf. Gielen et al., EMBO J. 8 (1989), 23–29) and are, in general, exchangeable as desired.

A large number of cloning vectors are available for preparing the introduction of foreign genes into higher plants, and these cloning vectors contain a replication signal for *E. coli* and a marker gene for the selection of transformed bacterial cells. Examples of such vectors are pBR322, pUC series, M13mp series, pACYC184. The desired sequence can be introduced into the vector at a suitable restriction cleavage site. The plasmid obtained is used for transforming *E. coli* cells. Transformed *E. coli* cells are grown in a suitable medium and then harvested and lysed. The plasmid is recovered. Analytical methods for characterizing the plasmid DNA obtained are, in general, restriction analyses, gel electrophoreses and other methods of biochemistry and molecular biology. After each manipulation, the plasmid DNA can be cleaved and DNA fragments obtained can be linked to other DNA sequences. Each plasmid DNA sequence can be cloned in the same or other plasmids.

A large number of techniques is available for introducing DNA into a plant host cell. These techniques encompass the transformation of plant cells with T-DNA using *Agrobacterium tumefaciens* or *Agrobacterium rhizogenes* as transformation agent, protoplast fusion, injection, DNA electroporation, the introduction of DNA by means of the biolistic method and the like.

When injecting and electroporating DNA into plant cells, the plasmid used need not meet any particular requirements. Simple plasmids such as, for example, PUC derivatives, may be used. If, however, whole plants are to be generated from such transformed cells, the presence of a selectable marker gene is required.

Depending on the method by which genes are introduced into the plant cell, other DNA sequences may be required. If, for example, the Ti or Ri plasmid is used for transforming the plant cell, at least the right hand side limit, but frequently the right and left hand side limit, of the Ti and Ri plasmid T-DNA must be linked, as a flanking region, with the genes to be introduced.

If agrobacteria are used for the transformation, the DNA to be introduced must be cloned into specific plasmids, viz. either into an intermediary vector or into a binary vector. The intermediary vectors can be integrated by homologous recombination into the Ti or Ri plasmid of the agrobacteria due to sequences which are homologous to sequences in the T-DNA. The Ti or Ri plasmid also contains the vir region which is required for transferring the T-DNA. Intermediary vectors cannot replicate in agrobacteria. The intermediary vector can be transferred to *Agrobacterium tumefaciens* by means of a helper plasmid (conjugation). Binary vectors are capable of replication both in *E. coli* and in agrobacteria. They contain a selection marker gene and a linker or polylinker which is framed by the left and right T-DNA border region. They can be transformed directly into the agrobacteria (Holsters et al. Mol. Gen. Genet. 163 (1978), 181–187). The agrobacterium which acts as the host cell should contain a plasmid which carries a vir region. The vir region is required for transferring the T-DNA into the plant cell; additional T-DNA may be present. This transformed agrobacterium is used for transforming plant cells.

The use of T-DNA for transforming plant cells has been described extensively in EP 120 516; Hoekema, in: The Binary Plant Vector System, Offsetdrukkerij Kanters B. V., Alblasserdam (1985), Chapter V; Fraley et al., Crit. Rev. Plant. Sci., 4, 146 and An et al. EMBO J. 4 (1985), 277–287.

To transfer the DNA into the plant cell, plant explants may advantageously be cocultured with *Agrobacterium tumefaciens* or *Agrobacterium rhizogenes*. Whole plants may be regenerated from the infected plant material (for example leaf sections, stem segments, roots, but also protoplasts or suspension-cultured plant cells) in a suitable medium which may contain antibiotics or biocides for selecting transformed cells. The resulting plants can then be tested for the presence of the DNA which has been introduced. Other possibilities of introducing foreign DNA using the biolistic method or by protoplast transformation are known (cf., for example, Willmitzer, L., 1993 Transgenic Plants. In: Biotechnology, A Multi-Volume Comprehensive Treatise (H. J. Rehm, G. Reed, A. Pühler, P. Stadler, eds.), Vol. 2, 627–659, VCH Weinheim).

Alternative systems for the transformation of monocotyledonous plants are the transformation by means of the biolistic approach, the electrically or chemically induced uptake of DNA into protoplasts, the electroporation of partially permeabilized cells, the macroinjection of DNA into inflorescences, the microinjection of DNA into microspores and proembryos, the DNA uptake by germinating pollen, and the DNA uptake in embyros by swelling (review: Potrykus, Physiol. Plant (1990), 269–273).

While the transformation of dicotyledonous plants via Ti-plasmid vector systems with the aid of *Agrobacterium tumefaciens* is well established, later publications suggest that even monocotyledonous plants are indeed accessible to transformation by means of Agrobacterium-based vectors (Chan et al., Plant Mol. Biol. 22 (1993), 491–506; Hiei et al., Plant J. 6 (1994), 271–282; Bytebier et al., Proc. Natl. Acad. Sci. USA 84 (1987), 5345–5349; Raineri et al., Bio/Technology 8 (1990), 33–38; Gould et al., Plant Physiol. 95 (1991), 426–434; Mooney et al., Plant Cell Tiss. & Org. Cult. 25 (1991), 209–218; Li et al., Plant Biol. 20 (1992), 1037–1048).

Three of the abovementioned transformation systems were established in the past for a variety of cereals: the electroporation of tissue, the transformation of protoplasts, and the DNA transfer by particle bombardment of regenerable tissue and cells (Jähne et al., Euphytica 85 (1995), 35–44).

The transformation of wheat is described in various references (review: Maheshwari et al., Critical Reviews in Plant Science 14 (2) (1995), 149–178), cf. also Hess et al. (Plant Sci. 72 (1990), 233), Vasil et al. (Bio/Technology 10 (1992), 667–674), Weeks et al. (Plant Physiol. 102 (1993), 1077–1084), and Becker et al. (Plant J. 5 (2) (1994), 299–307).

Once the DNA introduced is integrated in the genome of the plant cell, it is, as a rule, stable and is retained in the progeny of the originally transformed cell. It normally contains a selection marker which mediates resistance to a biocide such as phosphinothricin or an antibiotic such as kanamycin, G 418, bleomycin or hygromycin to the transformed plant cells. The marker, which is chosen individually, should therefore allow the selection of transformed cells over cells which lack the DNA introduced.

The transformed cells grow within the plant in the customary manner (see also McCormick et al., Plant Cell Reports 5 (1986), 81–84). The resulting plants can be grown normally and hybridize with plants which have the same transformed genetic material, or other genetic material. The resulting hybrids have the corresponding phenotypic characteristics. Seeds may be obtained from the plant cells.

Two or more generations should be grown in order to ensure that the phenotypic trait is stably retained and inherited. Also, seeds should be harvested to ensure that the relevant phenotype, or other characteristics, have been retained.

Another object of the invention are, furthermore, methods of generating a nucleic acid molecule according to the invention, wherein a nucleic acid molecule according to the invention is generated by a method known per se for the generation of nucleic acids. A wide range of different methods of isolating and cloning gene sequences are available to those skilled in cDNA cloning.

In addition, the sequence informations according to the invention can also be utilized for a multiplicity of other methods known to those skilled in the art, such as, for example, screening expression libraries for isolating genes using antibodies, or else for raising antibodies (polyclonal or monoclonal).

The entire plant chlD cDNA, preferably chlD from Nicotiana tabacum as shown in SEQ ID NO: 1, subsequences from SEQ ID NO: 1 or oligonucleotides derived from SEQ ID NO: 1 may be employed as probes for such methods, if appropriate those which selectively hybridize with other CHLD-encoding sequences from a library of cloned gene fragments of a selected organism, for example phototrophic microorganisms or mono- or dicotyledonous plants.

Such techniques include, for example, also the screening of genomic or cDNA libraries, cloned into suitable cells or viruses, and the amplification by means of polymerase chain reaction (PCR) using oligonucleotide primers derived from SEQ ID NO: 1.

The isolated chlD (sub)sequences according to the present invention can furthermore be modified or extended by standard methods of genetic engineering so as to obtain desired properties. To obtain selective hybridization under in-vitro or in-vivo conditions, chlD-specific probes have a length of at least 10 nucleotides, preferably at least 17 nucleotides.

Hybridization probes according to the present invention can be used, for example, to amplify or analyze CHLD-encoding sequences (i.e. CHLD-encoding nucleic acid molecules) from a selected organism by means of the PCR method, which is known to those skilled in the art, and can furthermore be used for isolating CHLD-encoding sequences from other organisms or as a diagnostic for detecting CHLD-encoding sequences in other organisms, or to identify and isolate modified CHLD-encoding sequences of a specific phenotype, such as, for example, resistance to herbicides, altered chlorophyll content, altered fitness, altered yield and the like.

The chlD-specific hybridiration probes can also be used to map the location of a naturally occurring chlD gene in a plant genome, using standard methods. These methods include, inter alia, identification of DNA polymorphisms and the use of such polymorphisms for analyzing the segregation of chlD genes in relation to other markers of known location. Mapping chlD genes may be of particular interest in plant breeding.

chlD-specific hybridization probes or CHLD-encoding (sub)sequences may also be exploited to inhibit expression of a chlD gene in planta (antisense technology).

Using standard methods, it is also possible to modify CHLD-encoding (sub)sequences or to extend them by novel sequence elements and to introduce them into the genome of plants. Plant transformation can be transient or stable, using conventional methods. The integration of sequences derived from chlD cDNA into the plant genome can be exploited for altering the properties of the plant, so that, for example, more or less functionally active Mg chelatase or a variant of Mg chelatase with altered properties is formed in the transgenic plant, or else that the expression level of the chlD gene in the transgenic plant is reduced. For example, the amount of functional Mg chelatase can be increased by standard methods if, for example, the chlD gene, alone or together with genes of other Mg chelatase subunits, is cloned into the transgenic plant under the transcriptional control of regulatory elements such as promoters and enhancers. An increased CHLD activity can be used, for example, for raising the chlorophyll content, which may be linked to higher yields, or to raise the tolerance to herbicides which inhibit chlorophyll biosynthesis. Also, for example cloning altered sequences according to the invention into transgenic plants, may be linked with a higher tolerance to herbicides.

The nucleic acid molecules which encode chlD sequences or fragments of these sequences (molecules) and which are introduced into transgenic plants can, however, also be provided with regulatory elements such as, for example, promoters and enhancers, in such a way that this results in lowering the original Mg chelatase activity in the transgenic plant (for example cosuppression, formation of chlD antisense RNA). A reduced Mg chelatase activity can be exploited for generating chlorotic plants or plants with chlorotic tissue. A reduced chlorophyll content may be desired, for example, when plants or plant organs are subjected to industrial processing at a later point in time, or when breeding for a variety of crops or ornamentals, for example vegetables such as chicory.

The present invention furthermore relates to a protein which has the biological function of a plant Mg chelatase subunit CHLD, preferably according to SEQ ID NO: 2, or a biologically active fragment thereof.

Another object of the invention is the use of a protein with the biological function of a plant Mg chelatase subunit CHLD, preferably according to SEQ ID NO: 2 or a biologically active fragment thereof, for determining the activity of an Mg chelatase and for raising antibodies.

Another object of the invention are methods of generating a protein with the function of a plant Mg chelatase subunit CHLD in a recombinant host cell, wherein this host cell is transformed with a nucleic acid molecule according to the invention encoding a plant Mg chelatase subunit CHLD or an active fragment thereof, preferably that a DNA sequence encoding a protein with the function of an Mg chelatase or a biologically active fragment thereof is inserted into an expression cassette suitable for the host cell, that the resulting expression cassette is inserted in a suitable manner into a vector suitable for the host cell, that a suitable host cell is transformed with the resulting vector and that the thus transformed host cell is grown in a suitable medium and that the protein which is produced by said host cell and which has the function of a plant Mg chelatase subunit CHLD is isolated in a suitable manner from the culture medium or from the host cell.

Yet another object of the present invention is a method of generating a protein with the function of a plant Mg chelatase or a biologically active fragment thereof in a recombinant host cell, wherein this host cell is transformed with a nucleic acid molecule according to the invention encoding a plant Mg chelatase or an active fragment thereof, preferably that a DNA sequence encoding a protein with the function of an Mg chelatase is inserted into an expression cassette which is suitable for the host cell; that the resulting expression cassette is inserted in a suitable manner into a vector suitable for the host cell, that a suitable host cell is transformed with the resulting vector; and that the host cell thus transformed is grown in a suitable medium and that the protein which is produced by said host cell and which has the function of a plant Mg chelatase is isolated in a suitable manner from the culture medium or the host cell.

In this sense, the present invention relates to the generation of plant Mg chelatase subunit CHLD and of plant Mg chelatase by genetic engineering. For example, to generate the proteins according to the invention in a host organism, the DNA sequences according to the invention can be cloned into an expression cassette which is suitable for heterologous expression of the structural gene in the selected host organism.

Examples of CHLD-encoding DNA sequences which are suitable for this purpose are the following: plant chlD cDNA, plant chlD cDNA molecules whose sequence has been altered by customary methods, but also synthetic DNA sequences which have been derived from plant chlD cDNA or plant CHLD protein or fragments thereof and which allow expression of a biologically active Mg chelatase CHLD. Moreover, it may be desired to introduce, into the expression cassette, specific regulatory sequences, for example promoters, operator sequences, enhancers, terminators, signal sequences, 5'- and 3'-untranslated sequences, or sequences encoding suitable fusion proteins. The use of regulatory sequences is generally customary technology, which can be varied within wide limits depending on the expression strategy. The resulting chlD expression cassette, provided with the necessary regulatory elements within the correct reading frame of the chlD structural gene, can be inserted into an expression vector with which the host organism selected can be transformed. Suitable expression strategies for generating recombinant proteins, and corresponding expression vectors, are generally known for host organisms such as, for example, *Escherichia coli*, insect cells and plant cells.

In general, the term "vector" refers to a suitable vehicle which is known to those skilled in the art and which allows the targeted transfer of a single- or double-stranded nucleic acid molecule into a host cell, for example into a DNA or RNA virus, a virus fragment, a plasmid construct which can be suitable for transferring nucleic acids into cells in the presence or absence of regulatory elements, metal particles as they can be employed, for example, in the particle-gun method, but it may also include a nucleic acid molecule which can be directly introduced into a cell by chemical or physical methods.

The recombinant organism obtained by stable or transient transformation for example with a chlD expression cassette can be used for obtaining recombinant Mg chelatase, preferably CHLD protein, or cell fractions containing CHLD. However, the recombinant organism may also directly be a component of an analytic test system.

It is also possible for the chlD structural gene together with the structural genes encoding the two other known subunits of Mg chelatase, namely CHLH (SEQ ID NO: 6) and CHLI (SEQ ID NO: 5) to be introduced into a host organism with the aid of conventional molecular-genetic processes, resulting in expression of a functional Mg chelatase in this host organism.

A preferred expression system is, for example, the use of bakers yeast (*Saccharomyces cerevisiae*) as host organism. Vectors which may be used are all known yeast vectors which have the suitable expression signals such as promoters, and suitable selection markers such as resistance genes or genes which complement for an auxotrophism.

The use of plant Mg chelatase is essentially based on its activity as a heterooligomeric enzyme complex, and this activity is directly linked to the presence of the subunit CHLD. Providing functionally intact plant Mg chelatase allows biochemical reactions to be performed not only in vitro (for example cell-free test system of Mg chelatase), but also in vivo, for example in uni- or multicellular recombinant organisms or cell cultures, in particular yeasts, bacteria, algae, insect cells or plants, and is therefore not limited to phototrophic organisms.

On the one hand, these reactions can be exploited for generating Mg-tetrapyrroles, on the other hand, these biochemical reactions can be used for determining, in a test system, the effect of chemical compounds, but also of heterogenous substance mixtures, relative to the function of Mg chelatase.

The present invention therefore furthermore relates to a method of determining the interaction between plant Mg chelatase subunits, which comprises transforming a host cell with a DNA sequence encoding a protein with the function of a subunit CHLD or with a biologically active fragment thereof and at least with one DNA sequence encoding a further subunit of Mg chelatase in such a manner that the interaction of the Mg chelatase gene products leads to a signal which can be measured directly or indirectly, qualitatively or quantitatively, preferably by activating a marker gene.

The method is suited for finding specific inhibitors or activators of plant Mg chelatase, allowing, inter alia, substances to be identified which have a potential herbicidal, growth-inhibitory or -enhancing or phytosanitary action.

The principle of these cellular (in-vivo) test systems is based on the fact that a recombinant organism which has been transformed with structure genes of plant Mg chelatase CHLD and which functionally expresses one or both of the other subunits of plant Mg chelatase indicates an essential function of one or more subunits in a manner which allows substances to be found which influence this function.

One function of Mg chelatase subunits consists in interacting with each other. This interaction leads to the formation of an enzyme complex and is a prerequisite for the enzyme function of Mg chelatase.

The present invention therefore relates to a test system which allows interaction of Mg chelatase subunit CHLD with one or two other subunits of the enzyme to be detected, and quantitatively determined, in vivo.

For example, interaction of subunit CHLD with the subunit CHLI can be measured in such a way that both subunits are linked with two other polypeptides or proteins in such a way that interaction of the subunits directly or indirectly causes a reaction in the cell which can be detected qualitatively and/or quantitatively.

Polypeptides which are suitable for this purpose are, for example, domains or subunits of regulatory proteins, for example from cellular signal transduction or transcription processes whose function is mediated via a protein-protein interaction.

Suitable are, for example, regulatory proteins of DNA transcription where the protein-protein interaction of two or more subunits can be detected with the aid of a reporter gene, so that the gene product of the reporter gene is formed only when two or more of the abovementioned subunits interact with each other.

To generate such a test system, for example one of the two Mg chelatase subunits to be tested can be fused to the DNA binding domain, while the other Mg chelatase subunit is fused to the transcription-activating domain of the regulatory protein. It is irrelevant here which of the two proteins is fused to which of the two domains. Thus, CHLD may be linked to the DNA binding domain and CHLI to the transcription-activating domain. This linkage can be mediated via the interaction of a further auxiliary factor, for example a protein-protein interaction or else protein-ligand interaction such as, for example, streptavidin-biotin. However, a covalent linkage, for example by fusion of encoding regions of genes in question, is preferred.

An example of such a regulatory protein is the gene product of the *Saccharomyces cerevisiae* GAL4 gene.

A host organism, into whose genome an indicator gene with the relevant promoter had already been integrated, is transformed with the abovedescribed fusion genes of Mg chelatase subunits. Such a host organism is distinguished by the fact that it expresses all functions of the transcription system used, with the exception of the regulatory protein intended to be expressed as recombinant protein. If a microorganism is used as the host organism, the recombinant organism can subsequently be isolated and multiplied as required using customary methods of microbiology and is therefore unlimited in its availability for use in the test system. Host organisms which are preferably used are therefore microorganisms which can be transformed and grown readily, such as, for example, yeast species or *E. coli*.

Furthermore, a promoter suitable for the transcription system is linked to a structural gene which encodes an indicator protein. This recombinant gene is distinguished by the fact that activation of the promoter directly or indirectly leads to expression of the indicator protein. Such an indicator protein is distinguished by the fact that it leads, in the recombinant organism, to a change which can be detected readily, for example by catalyzing pigment formation or a chemoluminescence reaction, by being colored or fluorescent itself, or by contributing to the growth of the microorganism.

The use of the described system in which transcription of an indicator gene is activated has the advantage over the growth test described further below In which a mutant is complemented with an Mg chelatase subunit that the former allows a more specific signal relative to an inhibitor of the enzyme or of an enzyme function, while the latter test first requires that cell growth inhibitors with a site of action other than Mg chelatase be excluded by control experiments. Thus, the present invention prefers the use of an indicator gene system to the growth test.

An example to be mentioned of such a system which puts into reality the abovementioned interactions with the aid of regulatory proteins of the transcription system is, in particular, the Matchmaker™ two-hybrid system by Clontech, Palo Alto, Calif., USA, Catalog No. #K 1605-1, 1995/96, which is hereby incorporated by reference.

To this end, plasmids are generated which cause the expression, in yeast cells, of CHL D, H and I as fusion proteins with the GAL4 binding domain and the GAL4 activation domain. To construct the expression plasmids, the DNA sections which encode the three Mg chelatase subunits are amplified by means of polymerase chain reaction (PCR).

The templates used for amplification are the plasmids which contain the cDNA of the genes in question. The PCR primers used are synthetic oligonucleotides which are distinguished by the fact that the sense primer shows homology to the 5' end, while the antisense primer shows homology to the 3' end of the gene in question. The primers may also be provided with restriction sites which facilitate cloning into the vector plasmid.

The preferred vectors used are the shuttle plasmids of the MATCHMAKER™ two-hybrid system (Clontech): pGBT9 and pAS2 each contain a gene which encodes the GAL4 activation domain. pGAD424 and pACT2 each contain a gene which encodes the GAL4 DNA binding domain. pGBT9 and pGAD424, and pAS2 and pACT2, respectively, are in each case used together in a system. pGBT9 and pGAD424 differ from pAS2 and pACT2 by the fact that the abovementioned genes are more weakly expressed in the first two cases than in the last two cases.

Each of the subunits encoding Mg chelatase are cloned individually into the vectors. Recombinant plasmids are introduced into E. coli by means of transformation, multiplied and isolated. In this manner, all 12 possible combinations of all three subunits with all four vectors are performed. The recombinant plasmids are termed as follows:

Gene CHL D in vector pAS2 was termed pCBS1148
Gene CHL D in vector pACT2 was termed pCBS1149
Gene CHL D in vector pGBT9 was termed pCBS1150
Gene CHL D in vector pGAD424 was termed pCBS1151
Gene CHL H in vector pAS2 was termed pCBS1152
Gene CHL H in vector pACT2 was termed pCBS1153
Gene CHL H in vector pGBT9 was termed pCBS1154
Gen CHL H in vector pGAD424 was termed pCBS1155
Gene CHL I in vector pAS2 was termed pCBS1156
Gene CHL I in vector pACT2 was termed pCBS1157
Gene CHL I in vector pGBT9 was termed pCBS1158
Gene CHL I in vector pGAD424 was termed pCBS1159

Then, a reporter yeast strain of the two-hybrid system is transformed with in each case two plasmids. A preferably used reporter yeast strain is a strain which expresses, as indicator protein, a GAL4-inducible beta-galactosidase, preferably strain SFY526 by Clontech. The two plasmids are selected in such a way that in each case one encodes a subunit in fusion with the DNA binding domain while the other encodes a subunit in fusion with the activation domain.

Yeast transformation is performed for example by the method of Klebe et al., 1983, Gene, 25, 333–341. To determine induction of the indicator gene, a yeast transformed with both plasmids is grown on solid medium and the activity of beta-galactosidase is determined after blotting onto filters using the method of Breedon and Nasmytl (Breedon, L. and Nasmyth, K. (1985) Regulation of the yeast HO gene. Cold Spring Harbor Symp. Quant. Biol. 50, 643–650).

Alternatively, the transformed yeast is grown in liquid medium and the beta-galactosidase activity is determined in yeast crude extract after cell disruption, using the method of Munder and Fürst (Munder, T. and Fürst, P. (1992). Mol. Cell. Biol. 12, 2091–2099).

To test substances, the recombinant organism is first grown in a suitable medium. The recombinant cells are then incubated together with the substance to be tested. The incubation conditions are selected in such a way that clearly measurable induction of the indicator gene takes place during the incubation time without the addition of substances to be tested. This can be effected for example by the incubation time extending over part of the growth phase.

Alternatively, induction may also be effected by expressing the proteins which play a role in transcription activation, with the aid of an inducible promoter. Induction of the indicator gene can be detected using customary detection reactions. If the indicator gene in the test system is activated, the consequence of gene activation is that a greater amount of reporter protein is formed in the host cells, than without activation of the indicator gene. The test system is preferably selected in such a way that the reporter protein is produced in at least twice the amount. Increase in production of the reporter protein by a factor of at least 10 is especially preferred. If the reporter protein is an enzyme, the enzyme activity can be determined by customary measuring methods, for example by colorimetry, fluorimetry or luminometry. For this purpose, intact cells or extracts therefrom of various degrees of purification may be incubated with a suitable chromogenic enzyme substrate. Incubation with the substrate can be affected as early as during incubation with the substance to be tested, or else afterwards.

If a chemical compound interferes with this interaction between the subunits, for example by binding to an "interface region" of the subunit, this compound inhibits the oligomerization process. Thus, this compound can reduce the amount of enzymatically active Mg chelatase in an organism and thus also have a potential herbicidal action. Thus, finding herbicidal compounds which inhibit the formation of the active Mg chelatase enzyme complex is also possible via the present test system.

To detect specific interaction of the substance with a protein of Mg chelatase, the substance must meet the following conditions:

1) In recombinant cells, a significantly lower induction of the indicator gene must take place after the substance has been added than in cells without substance added.
2) In an analogous transcription system (control system) in which the interaction of the Mg chelatase subunits was replaced by a different interaction, inhibition of the indicator reaction must only be marginally less or not measurable after addition of the substance. Any type of linkage, for example also covalent bonds of proteins, may be used as the other interaction.

If a substance meets the above conditions, it can be examined for its action in other test systems, for example in enzymatic tests with Mg chelatase, in plant cell cultures or in herbological tests on intact plants.

Moreover, an Mg chelatase gene can be introduced into a specific mutant of such an organism which is not capable of growth without function of the Mg chelatase in question, such as, for example, a photoautotrophic microorganism in which one or more Mg chelatase subunits have lost their function by mutation. The use of such a mutant has the particular advantage that growth of the recombinant organism in a suitable medium can thus be taken as a measure for the function of Mg chelatase and can thus quantitatively describe the effect of test substances on Mg chelatase. The growth test is distinguished by particularly simple handling and a rapid turnover of substances.

To this end, the plant chlD gene can be introduced into a mutant of an organism which is characterized in that it has an altered phenotype or is not capable of growth under certain culture conditions without function of the Mg chelatase, preferably without the function of the CHLD protein. Such a mutant can be generated for example by first altering, in a microorganism which requires the activity of an Mg chelatase for phototrophic growth, the structural genes for its own Mg chelatase in such a way that the functional enzyme with Mg chelatase activity is no longer formed, or not in sufficient amounts, so that the resulting organism is no longer capable of phototrophic growth. Furthermore, the plant structural genes chlI and chlH are expressed in this mutant. By additionally expressing the plant chlD structural gene, a functional plant Mg chelatase can be formed in the genetically engineered organism, and this plant Mg chelatase reimparts to this organism the capability of phototrophic growth. The growth of such a recombinant organism is then a direct measure of the plant Mg chelatase activity. A growth test with this recombinant organism makes it possible to determine whether the plant Mg chelatase is inhibited by a chemical compound added to the culture medium. To this end, the genetically engineered organism is grown in culture media under phototrophic culture conditions with and without the compound to be investigated. The chemical compound to be investigated is preferably employed in concentrations between $10^{-9}$ M and $10^{-3}$ M, especially preferably in concentrations between $10^{-7}$ M and $10^{-4}$ M.

To detect specific inhibition of the Mg chelatase by a chemical compound to be investigated and to exclude other modes of action as a cause for growth inhibition, the compound must meet the following criteria:
1) Growth of the genetically engineered organisms must be significantly poorer in the presence of the compound than in culture medium without the compound. 2) The compound must not significantly reduce growth of the same organisms under heterotrophic conditions.

Like growth, an altered phenotype of a suitably altered organism may also be used as indicator for catalytic activity of plant Mg chelatase. Various pigments of phototrophic microorganisms are made starting from the reaction product of Mg-chelatase, Mg-protoporphyrin. A recombinant microorganism constructed as described above which contains, instead of its own Mg chelatase, a recombinant plant Mg chelatase containing the recombinant CHLD protein, is only capable of forming its Mg-protoporphyrin-derived pigments when the plant Mg chelatase has sufficient activity. The pigmentation of such a recombinant organism is then a direct measure of plant Mg chelatase activity. Using this recombinant organism, analysis of the pigment composition makes it possible to determine whether the plant Mg chelatase is inhibited by a chemical compound which is added to the culture medium. To this end, the genetically engineered organism is grown in culture media with and without the compound to be investigated under culture conditions under which pigments synthesized from Mg-protoporphyrin are formed. The chemical compound to be investigated is preferably employed in concentrations between $10^{-9}$ M and $10^{-3}$ M, especially preferably in concentrations between $10^{-7}$ M and $10^{-4}$ M. To detect specific inhibition of the Mg chelatase by a chemical compound to be investigated and to exclude other modes of action as a cause for altered pigmentation, the compound must meet the following criteria:
1. The genetically engineered organisms show significantly lesser amounts of pigments formed starting from Mg-protoporphyrin, or an altered pigment composition, in the presence of the compound than in culture medium without the compound.
2. The compound must not significantly change pigment formation of the non-genetically-engineered starting organism under the same culture conditions.

If both criteria are met, it can be assumed that the compound examined is a specific inhibitor of plant Mg chelatase. If only condition 1, but not condition 2 is met, an enzymatic reaction of Mg chelatase makes it possible to determine whether the compound examined is a specific inhibitor of plant Mg chelatase.

If a substance meets the abovementioned conditions, it can be examined further for its action in the plant with or without further biochemical examinations directly either on intact plants or on suitable plant organs. The customary herbological and physiological methods may be used for this purpose. An essential prerequisite for various uses such as, for example, the generation of a biochemical test system for determining a protein function, is that the protein to be investigated can be obtained in the functional state and as pure as possible, i.e. free of interfering activities. As is the case with all cell proteins, this can be effected in the case of a plant Mg chelatase by isolating the individual subunits from plant tissue with the aid of customary protein purification processes. The present invention states that a functional plant Mg chelatase contains, besides the subunits CHLH and CHLI, the subunit CHLD, whose sequence, as an example, is given for Nicotiana tabacum in SEQ ID NO: 2. Isolation of a heterooligomeric protein whose activity is, moreover, also bound to a membrane fraction of the plant cell, as is the case with Mg chelatase, is generally considerably more difficult than isolation of a soluble or homooligomeric, or monomeric, enzyme since the protein loses its enzymatic activity in the course of the purification process, and this can subsequently only be restored by complicated methods. In addition, the enzymes of chlorophyll biosynthesis are formed as a function of the type of differentiation and of the developmental state of the cell. Moreover, these proteins, as is also the case with Mg chelatase, only represent a small part of the total cell protein so that particularly high concentration factors would have to be achieved when isolating them from plant tissue.

Due to the difficulties described, it is preferred according to the invention to use the Mg chelatase-encoding nucleic acid molecules for generating the recombinant plant Mg chelatase, especially preferably the recombinant Mg chelatase complex composed of the proteins CHLD, CHLH and CHLI. The recombinant plant CHLD protein may be very especially preferably mentioned.

Plant Mg chelatase generated by means of genetic engineering, preferably CHLD protein generated by means of genetic engineering, can be purified using a multiplicity of standard methods. Whether a method is suitable depends in each case on the host organism used, the expression strategy and other factors which are known to those skilled in the art of expression and purification of the recombinant proteins. In order to purify the recombinant protein, it may also be fused to other peptide sequences by altering its gene sequence in the expression cassette in a suitable manner. Fusion components to be used preferably are peptides or proteins which, as C- or N-terminal fusions, impart to the recombinant Mg chelatase subunits an affinity with certain column materials, or which allow the expression product to be located at a specific site within or outside of the cell, for example by means of transit or signal peptides or transit or signal sequences. Such fusions must not affect the function of Mg chelatase or must be capable of being cleaved off, for example by incorporating suitable protease cleavage sites. Examples which may be mentioned of fusion components are oligohistidine tails, the Strep-Tag™, glutathione-S-transferase (GST) or the maltose-binding protein (MalE), without this application being limited to the fusion components given by way of example or fragments thereof. To purify an active Mg chelatase complex, it may also suffice if only one of the subunits existing in the complex is fused to such a peptide or protein. Moreover, it is also possible to raise specific antibodies starting from already small amounts of Mg chelatase generated by a recombinant technology, preferably of the CHLD protein, and with the aid of these antibodies Mg chelatase or Mg chelatase subunits can be isolated from recombinant organisms or else from plants.

Generation of Mg chelatase, preferably of the CHLD protein, by means of genetic engineering, and their purification, allow for the first time a plant enzyme with Mg chelatase activity to be obtained in various degrees of purity, up to the pure Mg chelatase complex, composed of the subunits CHLD, CHLH and CHLI, or else the pure CHLD protein. A possible application for isolated or concentrated Mg chelatase is, for example, its use in biochemical test systems for determining the enzyme function.

The present invention furthermore relates to a method of determining the activity of plant Mg chelatase, where a protein is combined with a CHLD function with the gene products of the DNA sequences encoding for Mg chelatase subunits I and H in such a manner that the enzymatic activity of the Mg chelatase gene products leads to a directly or indirectly, qualitatively or quantitatively measurable signal.

The inhibitory effect of a chemical compound on Mg chelatase can be measured via a reduction in the typical catalyst activity of the enzyme or the complete inactivation of Mg chelatase in the presence of this compound. To this end, the plant Mg chelatase, composed of subunits CHLD, CHLH and CHLI, is incubated in a suitable reaction buffer together with its substrates protoporphyrin, ATP and $Mg^{2+}$.

By way of preferred reaction conditions, there may be mentioned a reaction buffer with a pH of between pH 4 and pH 11, preferably 5–10, in particular 6–9, and reaction temperatures between 2 and 50° C., preferably 10–40° C. and the like.

Quantification of the enzyme inhibition can be effected by a simple comparison of the catalytic activity of Mg chelatase in the absence and presence of the chemical compound to be investigated.

To determine the Mg chelatase activity, a variety of biochemical measuring methods may be employed, by means of which either the formation of the reaction products of the Mg-chelatase-catalyzed reaction is measured, for example, Mg-protoporphyrin, ADP or phosphate, or else a decrease in concentration of the enzyme substrates of Mg chelatase is measured, for example protoporphyrin, ATP or $Mg^{2+}$. A large number of standard methods for determining Mg chelatase activity are available to those skilled in the art of performing enzyme tests. Methods which may preferably be mentioned are those for measuring the conversion rate of protoporphyrin to Mg-protoporphyrin in the reaction batch by measuring the different fluorescence properties of Mg-protoporphyrin and protoporphyrin (for example Walker et al., Plant Physiol. Biochem. 30:263–269 (1992)) or by photometric analysis of the altered absorption resulting from the conversion of protoporphyrin to Mg-protoporphyrin (for example Gorchein, Biochem. J. 299:869–874 (1991)) or by quantifying protoporphyrin or Mg-protoporphyrin by HPLC analysis. Determining the ATPase activity of Mg chelatase may be mentioned as a further preferred measuring method, and here it is possible to detect, for example, the formation of phosphate by a phosphate detection, for example by the methods based on the system described by Fiske et al., J. Biol. Chem 66:375–400 (1925). In addition, the inhibitory type of a chemical compound relative to plant Mg chelatase can be determined by varying the concentrations of the substrate and the inhibitory substance, using customary biochemical methods.

Instead of using purified Mg chelatase, it is also possible to use intact cells of the recombinant organism which gives recombinant expression of the three Mg chelatase subunits CHLD, CHLH and CHLI, or protein-containing extracts from this organism, or Mg-chelatase-containing fractions from this organism which have been concentrated to different degrees. Yeast cells may be mentioned as the preferred recombinant host organism for this purpose. Alternatively, it is also possible to use a functional Mg chelatase containing the subunits CHLD, CHLH and CHLI which has been isolated from plant tissue or plant cell cultures.

If, with the aid of the biochemical or cell-biological test systems, it is found that a chemical compound inhibits plant Mg chelatase in vitro, this compound can be investigated directly for its action on plants, either on intact plants or on suitable parts of plants. To this end, a multiplicity of conventional herbological and physiological methods are available to those skilled in the art assessing active substances on plants.

Moreover, the Mg chelatase generated by means of genetic engineering, preferably an Mg chelatase complex with the subunit CHLD which has been generated by means of genetical engineering, or else the free subunit CHLD, can also be used for example for elucidating the spatial structure of the plant enzyme. Generally known methods such as, for example, X-ray structural analysis of protein crystals or NMR spectroscopy may be used for elucidating the spatial structure. The structure information on Mg chelatase, preferably on the subunit CHLD, can be used, for example, for rationally designing novel Mg chelatase inhibitors, and thus potential herbicides.

The disclosures in German patent application 197 17 656.9 from which this application claims priority, and in the abstract accompanying this application are incorporated herein by reference.

The examples which follow are intended to illustrate the invention in greater detail and are in no way to be understood as a limitation:

Standard methods such as DNA and RNA isolation, sequence analysis, restriction, cloning, gel electrophoresis, radio labeling, Southern and Northern blot were carried out by conventional methods (Sambrook at al., 1989 Molecular Screening: A laboratory manual $2^{nd}$ ed. Cold Spring Harbour Laboratory Press N.Y. USA; Sanger et al., 1977, Proc. Natl. Acad. Sci. USA 74, 5463–5467).

EXAMPLE 1

Cloning a Tobacco cDNA Which Encodes the Mg Chelatase Subunit CHLD

To identify the tobacco chlD cDNA, the peptide sequences VDASGS (SEQ ID NO: 3), TDGRGN (SEQ ID NO: 4) and AKGAVM (Seq. ID NO: 7) were selected which correspond to the protein sequences derived from the chlD gene of Synechocystis PCC6803 (Jensen et al. (1996) J. Biol. Chem. 271, 16662–16667) to prepare the following mixture of DNA primer sequences:

ga(c/t)gt(a/c/t/g)ga(g/a)aa(a/g)(t/a)c(a/c/g/t)gt(a/c/g/t) (SEQ ID NO: 8)

at(a/g)tt(a/c/t/g)cc(a/c/t/g)cg(a/c/t/g)cc(a/g)tc(a/c/t/g)g (SEQ ID NO: 9)

gc(a/c/t/g)aa(a/g)gg(a/c/t/g)gc(a/c/t/g)gt(a/c/t/g)atgc (SEQ ID NO: 10)

These primers were used in a polymerase chain reaction (PCR) to amplify the genomic DNA from the Synechocystis PCC6803: 2 cycles with in each case 1 min. 94°, 2 min. 45° C., 3 min. 72° C., then 28 cycles in each case 30 sec. 94° C., 90 sec. 60° C., 2 min. 72° C.

The PCR resulted in a DNA fragment of approx. 270 bp which was cloned into the cloning vector pCRTMII (Invitrogen, San Diego) and isolated for further handling by means of a restriction digest.

The isolated and $^{32}$P[dCTP]-labeled fragment of approx. 270 bp in length was used as a hybridization probe to screen a lambda ZAP II cDNA library of tobacco (Nicotiana tabacum SR1, Stratagene) following the instructions.

The DNA present after a cDNA library screening in the phagemid pBluescript SK was isolated and sequenced. The chlD cDNA sequence identified and shown in SEQ ID NO: 1 contains an open reading frame 2274 nucleotides in length, and untranslated regions on the 5' and 3' termini.

Genomic tobacco DNA was hybridized with radio labeled DNA of the CHLD gene. To this end, the CHLD gene was excised from the phagemid pBluescript SK using EcoRI and HindIII. The resulting two fragments of sizes 2069 bp and 426 bp were radio labeled using $^{32}$P(dCTP).

EXAMPLE 2

Generation of chlD Antisense Tobacco Plants

The tobacco cDNA fragment for CHLD which was obtained according to Example 1 in pBluescript SK—was excized from the vector pBluescript SK-using KpnI and XbaI and ligated into the binary vector BinAR (Höfgen and Willmitzer, Plant Science (1990) 66, 22–230) which had been cleaved with KpnI and XbaI.

First, E. coli strain DH 5 α was transformed with the construct and then Agrobacterium tumefaciens strain GV 2260. Using the leaf-disk transformation method (Horsch et al., Science 228, 1229–31), young tobacco leaf disks were incubated with the agrobacteria, and the CHLD antisense gene was stably-integrated into the plant genome.

EXAMPLE 3

Generation of the chlD Sense Tobacco Plants

To generate the chlD sense tobacco plants, the chlD cDNA was excized from p Bluescript SK-using SmaI and XbaI and cloned into the BinAR vector after having been subjected to restriction digest. To stably integrate it into the tobacco genome, the method described in Example 2 was chosen.

EXAMPLE 4

Figure 1B:
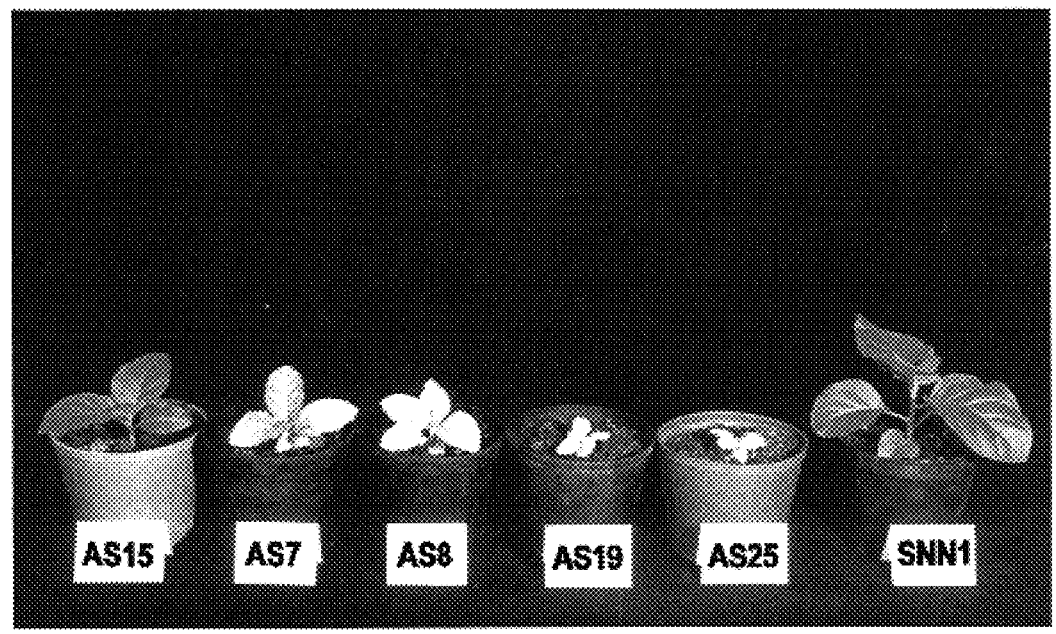
Figure 1C:
Figure 1D:
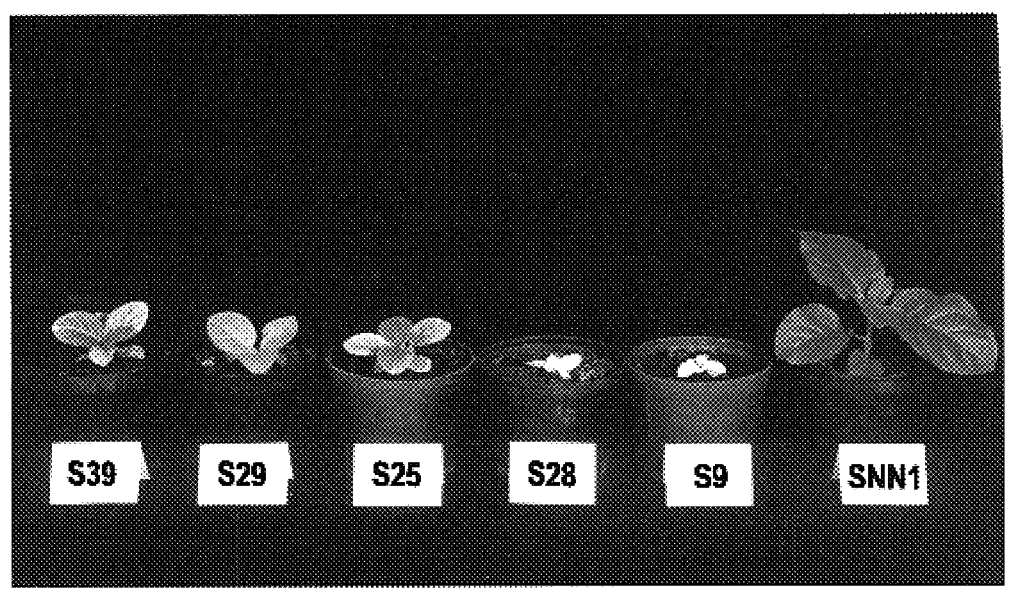

Analysis of the Transgenic Tobacco Plants 67 sense plants and 56 antisense plants were isolated. The transgenic plants with antisense or sense genes for CHLD showed gradually different chlorophyll deficiencies. Chlorotic leaves showed a variety of variation patterns. There were uniformly decolorized, yellowish-green leaves, leaves with differently pigmented spots, and leaves with white areas along the leaf veins and green intercostal areas. As the leaves aged, they lost chlorophyll. Plants with reduced chlorophyll content also showed reduced growth (see FIG. 1a to 1d).

Moreover, the stable integration of the sense or antisense chlD genes into the genome of tobacco plants was confirmed by Southern blot analysis, and the mRNA content of the chlD transcript was determined by Northern blot analysis. In the antisense plants, the content is reduced in comparison with the wild type. In comparison with the wild type, chlD sense plants only have slightly elevated chlD mRNA contents.

The Mg chelatase activity was determined for transgenic and wild-type plants by the method of Lee et al. (1992, Plant Physiol. 99, 1134–1140). The sense and antisense plants always show reduced enzyme activities.

The phenomenon of the reduced enzyme activities in the supposedly CHLD-overexpressed transformants can be explained by negative dominance. An oversupply of the CHLD subunit causes a disruption of the finely regulated construction of the Mg chelatase enzyme complex.

The protoporphyrin IX and chlorophyll content was determined in transgenic and wild-type plants (see Table 2). It must be emphasized that the transformants with sense or antisense CHLD mRNA show, as a rule, protoporphyrin contents in their young leaves tested (leaf 3, 5 and 7) which are up to 3–5 times higher than those of the wild-type plants.

The determination of the chlorophyll content confirms the macroscopic phenotype. In individual plants, the content was reduced by up to 25%.

TABLE 2

Relative protoprophyrin IX and chlorophyll content in sense and antisense plants

| Plant | Leaf | Protoporphyrin IX [%] | Chlorophyll [%] |
|---|---|---|---|
| SNN | 3 | 100 | 100 |
|  | 5 | 100 |  |
|  | 7 | 100 | 100 |
| AS7 | 3 | 584 | 25 |
|  | 5 | 542 |  |
|  | 7 | 157 | 28 |
| AS9 | 3 | 135 | 50 |
|  | 5 | 120 | — |
|  | 7 | — | 49 |
| AS13 | 3 | 160 | 78 |
|  | 5 | 102 | — |
|  | 7 | 115 | 78 |
| AS18 | 3 | 374 | 74 |
|  | 5 | 470 | — |
|  | 7 | 295 | 80 |
| AS21 | 3 | 231 | 95 |
|  | 5 | 188 | — |
|  | 7 | 98 | 101 |
| S1 | 3 | 189 | 78 |
|  | 5 | 262 | — |
|  | 7 | 297 | 80 |
| S20 | 3 | 423 | 32 |
|  | 5 | 293 | — |
|  | 7 | 144 | 25 |
| S22 | 3 | 189 | 117 |
|  | 5 | 151 | — |
|  | 7 | 115 | 94 |
| S29 | 3 | 298 | 25 |
|  | 5 | 265 | — |
|  | 7 | 137 | 26 |

TABLE 2-continued

Relative protoprophyrin IX and chlorophyll content in sense and antisense plants

| Plant | Leaf | Protoporphyrin IX [%] | Chlorophyll [%] |
|-------|------|-----------------------|-----------------|
| S38   | 3    | 257                   | 120             |
|       | 5    | 127                   | —               |
|       | 7    | —                     | 107             |

SNN = Wild type
S = Sense
As = Antisense

EXAMPLE 5

Construction of Plasmids for Expressing CHL D, H and I as Fusion Proteins With the GAL4 Binding Domain and the GAL4 Activation Domain To construct the expression plasmids, the DNA encoding the three Mg chelatase subunits was amplified by means of polymerase chain reaction (PCR).

To amplify the chlD gene, 100 ng of plasmid pNTCHLD were used as template. The following two oligonucleotides were used as PCR primers: 5'-TGA CCC GGG GGT AGT GGA ACC TGA AAA ACA ACC-3' (SEQ ID NO: 10) as sense primer with SmaI restriction site, and either 5'-GGC GAA TTC TCA AGA TTC CTT TAA TGC AGA TAA-3' (SEQ ID NO: 12) with EcoRI restriction site or 5'-GCG GTC GAC TCA AGA TTC CTT TAA TGC AGA-3' (SEQ ID NO: 13) with SalI restriction site as antisense primer.

To amplify the CHLH gene, 100 ng of plasmid pNTCHLH were used as template. The following two oligonucleotides were used as PCR primers: 5'-GCT GAT ATC GGC TAT TGG CAA TGG TTT ATT CAC-3' (SEQ ID NO:14) with EcoRV restriction site as sense primer and 5'-GCG TCG ACA TTT ATC GAT CGA TTC CCT CAA-3' (SEQ ID NO: 15) with SalI restriction site as antisense primer. To amplify the chlI gene, 100 ng of plasmid PNTCHLI were used as template. The following two oligonucleotides were employed as PCR primers: 5'-CAG CCC GGG GGG TCC ACT ACT AGG-3' (SEQ ID NO: 16) with SmaI restriction sites sense primer and 5'-CAG GTC GAG GCA CAG TAC AAA GCC-3' (SEQ ID NO: 17) with SalI restriction site as antisense primer.

The shuttle plasmids of MATCHMAKER™ two-hybrid system (Clontech) were used as vectors: pGBT9 and pAS2 each contain a gene which encodes the GAL4 activation domain. pGAD424 and pACT2 each contain a gene which encodes the GAL4 DNA binding domain. pGBT9 and pGAD424, and pAS2 and pACT2, respectively, are in each case used together in a system. pGBT9 and pGAD424 differ from pAS2 and pACT2 by the fact that the abovementioned genes are more weakly expressed in the first two cases than in the last two cases.

To clone chlD into vector pACT2, the gene was amplified by means of the sense primer with SmaI cleavage site and the antisense primer with EcoRI cleavage site and subsequently ligated with the SmaI- and EcoRI-cut vector.

To clone chlD into in each case one of vectors pAS2, pGBT9 and pGAD424 the gene was amplified by means of the sense primer with SmaI cleavage site and the antisense primer with SalI cleavage site and subsequently ligated with the SmaI- and SalI-cut vector.

To clone in each case one of genes chlH and I into in each case one of vectors pAS2, pGBT9 and pGAD424, the genes were amplified in each case by means of the sense and the antisense primer and subsequently ligated with the vectors cut in each case with SmaI and SalI.

To clone in each case one of genes chlH and I into vector pACT2, the genes were amplified by means of the sense and the antisense primer and subsequently ligated with the SmaI- and XhoI-cut vector. The ligated DNA vias introduced into E. coli DH 5a by means of transformation, and transformed clones were selected on agar medium with 100 μg ampicillin/ml. Plasmid DNA was isolated from the recombinant bacteria and tested for identity by means of restriction analysis.

All 12 possible combinations of all three subunits with all four vectors were made in this manner.

EXAMPLE 6

Determining the Interaction Between Mg Chelatase Subunits by Means of the Two-hybrid System in Yeast β-Galactosidase liquid assay in yeast (Munder and Fürst, 1992, Mol.Cell.Biol. 12, 2091–2099) using strain SFY526+pAS2-chlD+pACT2-chlI as example.

Competent yeast cells strain SFY 526 (Harper et al., 1993, Cell, 75, 805–816) were made by the method of Klebe (Klebe et al., 1983, Gene, 25, 333–341) and transformed with the plasmids given in Example 2. SFY 526 was transformed with all plasmids individually and in all possible combinations and selected on minimal agar (1.5% agar, 10% YNB glucose) with an addition of amino acids (adenine 20 mg/l; L-histidine.HCl 20 mg/l; L-lysine.HCl 30 mg/l; L-leucine 30 mg/l; L-tryptophane 20 mg/l).

The yeast strain SFY526+pAS2-chlD+pACT2-chlI to be measured was grown in 10 ml of minimal medium (10% of YNB glucose) with an addition of amino acids required (adenine 20 mg/l; L-histidine HCl 20 mg/l and L-lysine HCl 30 mg/l) overnight at 30° C. and 180 rpm in a sterile 50 ml wide-necked flask with metal cap. The optical density ($OD_{600}$) of this overnight culture was recorded (Beckman DU 640 spectrophotometer), and the values measured were between 1.0 and 2.0.

100 μl of this culture were tested for β-galactosidase activity. The total sample volume was approx. 1 ml:

100 μl culture
700 μl Z buffer+mercaptoethanol
50 μl trichloromethane
50 μl 0.1% SDS A zero-value was examined in parallel:

700 μl Z buffer
50 μl trichloromethane
50 μl 0.1% SDS

Sample and parallel zero value were each vortexed for 30 seconds, and 160 μl of ONPG solution(4 mg o-nitrophenyl-β-$_D$-galactopyranoside on 1 ml of Z buffer+mercaptoethanol) was added to each of them. The samples were then shaken carefully and incubated in a water bath at 30° C. After one hour, the reaction was quenched by adding 400 μl of 1M $Na_2CO_3$, and the samples were spun for 10 minutes at 13,000 rpm (Heraeus Biofuge fresco, fixed-angle rotor 24). The supernatant was measured at 420 nm against the zero-value (Beckman DU 640 spectrophotometer), and the β-galactosidase activity was calculated:

U=1000 $E_{420}$ $(CVt)^{-1}$ $E_{420}$ is the extinction at 420 nm, C is the density of the cell suspension ($OD_{600}$), V is the cell suspension volume employed, and t is the incubation time.

The measurement was repeated on two further clones, and the mean was determined.

Solutions required:

Z buffer 1000 ml:
  16.1 g Na$_2$HPO$_4$x7H$_2$O
  5.5 g NaH$_2$PO$_4$x7H$_2$O
  0.75 g KCl
  MgSO$_4$x7H$_2$O Z buffer+mercaptoethanol (make freshly)
100 ml of Z buffer+270 µl mercaptoethanol

EXAMPLE 7

Reconstitution Assay Mg Chelatase Activity in Yeast (Willows et al., 1996, Eur.J.Biochem. 235, 438–443) Strain SFY526+pAS2-chlD+pACT2-chlH+pSG28

Competent cells of strain SFY526+pAS2-chlD+pACT2-chlH were prepared (Klebe et al.; 1983; Gene, 25, 333–341) and transformed with pSG28 (p423TEF+chlI; p423 TEF: Mumberg et al.; 1995; Gene, 156;119–122). Transformants were selected on minimal agar (10% YNB glucose; 1.5% agar) with an addition of adenine (20 mg/l) and L-lysine.HCl (30 mg/l). 15 ml of a preculture (minimal medium: 10% YNB glucose+20 mg/l adenine+30 mg/l L-lysine HCl) of this strain were grown for 24 hours at 30° C. and 180 rpm in a sterile 50 ml wide-necked flask with metal cap. 150 ml of main culture (minimal medium: 10% YNB glucose+20 mg/l adenine+30 mg/l L-lysine HCl) were inoculated with 7.5 ml of preculture and shaken for 20 hours at 30° C. and 180 rpm using a sterile 500 ml Erlenmeyer flask with cottonwool plug. The cells were sedimented for 5 minutes at 5000 rpm (Sigma 4K 10) and resuspended in 1.5 ml of assay buffer (0.1 M tricine pH 7.9, 0.3 M glycerol, 25 mM MgCl$_2$, 4 mM DTT). This cell suspension was subsequently disrupted ultrasonically for 3x30 seconds on ice at low ultrasonic strength.

The disrupted cells were sedimented for 15 minutes at 5000 rpm (Sigma 4 K 10) and the supernatant was processed further. The protein content of this yeast extract was determined using the BioRad protein assay by the method of Bradford.

The assay volume was 1 ml. 1 ml of assay buffer contained 1 mg of protein extract of the disrupted yeast culture, 4 mM ATP, 1.5 µM protoporphyrin IX, 50 mM phosphocreatine and 10 U creatinephosphokinase.

This incubation mix was incubated for one hour in the dark at 30° C., and a fluorescence emission spectrum between 500 and 650 nm at an excitation wavelength of 420 nm was then recorded in a Perkin Elmer luminescence spectrometer LS50 B and subjected to HPLC analysis.

---

We claim:

1. An isolated nucleic acid molecule that specifically hybridizes to SEQ ID NO: 1 or a fragment or a complement thereof, wherein the nucleic acid molecule encodes a plant magnesium (Mg) chelatase subunit CHLD.

2. The nucleic acid molecule as claimed in claim 1 comprising SEQ ID NO: 1, which encodes a plant Mg chelatase subunit CHLD.

3. The nucleic acid molecule as claimed in claim 1 which encodes a protein shown as SEQ ID NO: 2.

4. An isolated nucleic acid molecule of at least 10 nucleotides in length which hybridizes specifically with the nucleic acid molecule as claimed in claim 1.

5. An isolated nucleic acid molecule which encodes a plant peptide selected from the group consisting of SEQ ID NO: 3, SEQ ID NO: 4 and SEQ ID NO: 7.

6. An isolated nucleic acid molecule that is an antisense or complementary sequence of the nucleic acid molecule as claimed in claim 1.

7. A method of isolating or identifying a nucleic acid molecule encoding a protein with the function of a plant Mg chelatase subunit CHLD or a biologically active fragment thereof comprising isolating or identifying a nucleic acid molecule which specifically hybridizes to the isolated nucleic acid as claimed in claim 1 and which encodes a functional Mg chelatase subunit CHLD.

8. A method of generating a protein with the function of a plant Mg chelatase subunit CHLD comprising:
   i. transforming a host cell with a nucleic acid molecule according to claim 1;
   ii. growing the host cell in a suitable medium;
   iii. expressing the nucleic acid molecule encoding a plant Mg chelatase subunit CHLD or a biologically active fragment thereof; and
   purifying the plant Mg chelatase subunit CHLD or biologically active fragment thereof in a suitable manner from the culture medium or from the host cell.

9. A method of generating a plant Mg chelatase comprising:
   i. transforming a host cell with a nucleic acid molecule according to claim 1 and at least one nucleic acid molecule encoding a further plant Mg chelatase subunit;
   ii. growing the host cell in a suitable medium;
   iii. expressing the nucleic acid molecules encoding the plant Mg chelatase subunits; and
   iv. purifying the plant Mg chelatase or biologically active fragment thereof in a suitable manner from the culture medium or from the host cell.

10. A purified recombinant protein having the function of a plant Mg chelatase subunit CHLD.

11. The purified protein as claimed in claim 10, which comprises SEQ ID NO: 2.

12. A method for determining Mg chelatase activity comprising measuring the activity of the purified protein as claimed in claim 10 in a suitable expression system.

13. A non-naturally occurring chimeric gene comprising a promoter functionally fused to the nucleic acid molecule as claimed in claim 1.

14. A vector comprising a nucleic acid molecule as claimed in claim 1.

15. A recombinant host cell which expresses a nucleic acid molecule as claimed in claim 1.

16. A transgenic plant, transgenic plant cells, transgenic plant organs, transgenic plant seeds, or transgenic propagation material comprising a nucleic acid molecule as claimed in claim 1.

17. The recombinant host cell according to claim 15, which is stably transformed with the vector of claim 14.

* * * * *